(12) United States Patent
Aalto et al.

(10) Patent No.: US 9,469,583 B2
(45) Date of Patent: Oct. 18, 2016

(54) COMPOSITION COMPRISING PARAFFIN FRACTIONS OBTAINED FROM BIOLOGICAL RAW MATERIALS AND METHOD OF PRODUCING SAME

(71) Applicant: Neste Oil Oyj, Espoo (FI)

(72) Inventors: Pekka Aalto, Porvoo (FI); Kati Sandberg, Järvenpää (FI); Tomi Nyman, Vantaa (FI); Maija Hakola, Helsinki (FI)

(73) Assignee: NESTE OYJ, Espoo (FI)

( * ) Notice: Subject to any disclaimer, the term of this patent is extended or adjusted under 35 U.S.C. 154(b) by 352 days.

(21) Appl. No.: 14/147,243

(22) Filed: Jan. 3, 2014

(65) Prior Publication Data

US 2015/0191404 A1    Jul. 9, 2015

(51) Int. Cl.
*C07C 6/00* (2006.01)
*C07C 7/05* (2006.01)
(Continued)

(52) U.S. Cl.
CPC . *C07C 9/14* (2013.01); *C07C 1/22* (2013.01); *C09D 7/001* (2013.01); *C10G 3/42* (2013.01); *C10G 3/50* (2013.01); *C10G 45/58* (2013.01); *C10G 65/043* (2013.01); *C10L 1/04* (2013.01); *C10M 105/00* (2013.01); *C10M 177/00* (2013.01); *C10G 2300/1011* (2013.01); *C10L 2200/0469* (2013.01); *C10L 2270/08* (2013.01); *C10M 2203/003* (2013.01); *C10N 2220/021* (2013.01); *C10N 2220/025* (2013.01); *C10N 2220/028* (2013.01); *C10N 2220/031* (2013.01); *C10N 2240/201* (2013.01);

(Continued)

(58) Field of Classification Search
CPC ........ C07C 9/14; C07C 1/22; C10M 177/00; C10M 105/00; C10M 2203/003; C10L 1/04; C10L 2270/08; C10L 2200/0469; C10G 65/043; C10G 3/42; C10G 3/50; C10G 45/58; C10G 2300/1011; C09D 7/001; Y02P 20/582; Y02P 30/20; C10N 2220/021; C10N 2220/03; C10N 2220/025; C10N 2220/028; C10N 2240/201; C10N 2220/031; C10N 2240/40
USPC ...................................... 585/1, 14, 240–242
See application file for complete search history.

(56) References Cited

U.S. PATENT DOCUMENTS 8,067,657 B2    11/2011  Duarte Santiago et al.
8,309,065 B2    11/2012  Ansmann et al.
(Continued)

FOREIGN PATENT DOCUMENTS

EP    2 368 967 A1    9/2011
FI    EP 2368967 A1 *  9/2011  ................ C10L 1/08
JP    6-346047 A       12/1994

OTHER PUBLICATIONS

New Binary Alkane Mixtures as PCMS for Cooling Applications by Yilmaz, S.,Sayin, O, Ozgul, Gok, O, Yilmza, M, Beyhan, B, Saha, N, Paksov, H and Evilya, H (available online Apr. 19, 2009).*

(Continued)

*Primary Examiner* — Pamela H Weiss
(74) *Attorney, Agent, or Firm* — Buchanan Ingersoll & Rooney PC

(57) ABSTRACT

A composition, including 40-50 wt-% C14 paraffins, based on the total weight of the composition, and 35-45 wt-% C15 paraffins, based on the total weight of the composition, wherein the C14 and C15 paraffins are produced from a biological raw material.

16 Claims, 5 Drawing Sheets

(51) Int. Cl.
*C10G 3/00* (2006.01)
*C10M 105/00* (2006.01)
*C10L 1/04* (2006.01)
*C07C 9/14* (2006.01)
*C07C 1/22* (2006.01)
*C09D 7/00* (2006.01)
*C10G 45/58* (2006.01)
*C10G 65/04* (2006.01)
*C10M 177/00* (2006.01)

(52) U.S. Cl.
CPC ......... *C10N 2240/40* (2013.01); *Y02P 20/582* (2015.11); *Y02P 30/20* (2015.11)

(56) References Cited

U.S. PATENT DOCUMENTS

| | | |
|---|---|---|
| 2003/0211949 A1 | 11/2003 | Guyomar et al. |
| 2006/0207166 A1 | 9/2006 | Herskowitz et al. |
| 2007/0260102 A1 | 11/2007 | Duarte Santiago et al. |
| 2008/0302001 A1 | 12/2008 | Koivusalmi et al. |
| 2013/0109893 A1 | 5/2013 | Robota et al. |

OTHER PUBLICATIONS

Sasol Linear Paraffins Apr. 13, 2012.*
EIC Search Feb. 2, 2016.*
Sinthavarayan, "Fractionation and Characterization of Renewable Paraffinic Solvents" Thesis submitted in partial fulfillment of the requirements of the degree of Master of Science in Technology, Aalto University School of Chemical Technology, Environomical Pathways for Sustainable Energy Systems (SELECT) Master's Program, Espoo, Finland, Aug. 1, 2013, pp. 1-121 and Appendices A-L.
Joshua Stuart: "Linear Paraffins", Sasol, Mar. 11 2009, p. 1-1, XP002742078, Retrieved from the internet: http://www.sasoltechdata.com/MarketingBrochures/paraffins.pdf.
Database WPI, Week 199510, Thomson Scientific, London, GB, AN 1995-070534, XP002742077, Dec. 20, 1994.
International Search Report and Written Opinion issued in corresponding International Application No. PCT/IB2014/003235 mailed Aug. 7, 2015.

* cited by examiner

COMPOSITION COMPRISING PARAFFIN FRACTIONS OBTAINED FROM BIOLOGICAL RAW MATERIALS AND METHOD OF PRODUCING SAME

FIELD

The present disclosure relates to a composition comprising paraffin fractions obtained from biological raw materials and to a method for producing said fractions.

BACKGROUND INFORMATION

Solvents have been playing important roles in many applications, for example, in paints and coatings, printing inks, adhesives, cosmetics, and pharmaceuticals. Global solvents utilization is around 20 million tonnes in 2011 and demand is predicted to grow an average of 2.5% annually. The demand may be expected to reach 25 million tonnes in 2019 with expected revenues increasing to 25 billion euros.

Aliphatic solvents are one of the solvent groups which can refer to hydrocarbon solvents comprising paraffins (straight chains), isoparaffins (branch chains) and naphthenes (non-aromatic rings). Aliphatic solvents account for more than 2.64 million tonnes in 2011, or around 13% of global solvents consumption. Aliphatic solvents are mainly produced from crude oil. They can be produced through several physical processes used in petrochemical industry starting from crude oil distillation, cracking, alkylation, isomerization, reforming and other operations.

Several separation techniques are available such as, for example, distillation, absorption, liquid-liquid extraction, drying, leaching, crystallization and gas adsorption. However, 95% of liquid separations are conducted by distillation processes. This is due to the fact that other alternative separation techniques, such as absorption, adsorption, and extraction, can require the addition of an external substance, for example, entrainer, solvent and adsorbent to create two phases for separation. This external substance has to then be removed. While in the distillation, the principle is based on the difference in composition between liquid mixture and the vapor formed by different volatilities of the components presented in the mixtures. Moreover, distillation can be the least expensive of possible methods for separating a given mixture, and in many cases it is the only feasible method.

SUMMARY

According to an exemplary aspect, a composition is provided, comprising: 40-50 wt-% C14 paraffins, based on the total weight of the composition, and 35-45 wt-% C15 paraffins, based on the total weight of the composition, wherein the C14 and C15 paraffins are produced from a biological raw material.

According to an exemplary aspect, a process for producing an exemplary composition is provided, the process comprising: conducting hydrodeoxygenation and isomerization processes of a biological raw material; and conducting a separation process of the resulting material, wherein the separation process includes distillation.

DETAILED DESCRIPTION

Figure 1:
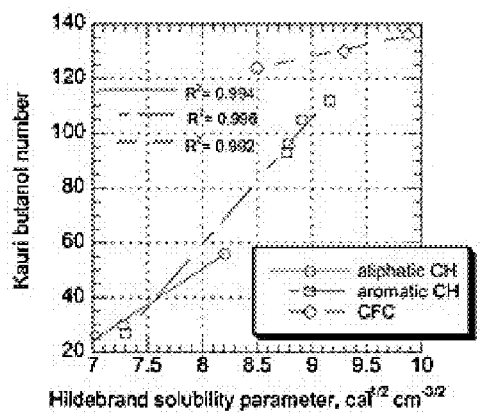
FIG. 1 depicts a graph of Kauri butanol number vs. Hidebrand solubility parameter, according to an exemplary aspect.

The present disclosure is related to compositions comprising paraffins produced from biological raw materials. The compositions can be used as solvents or solvent components and in various applications including but not limited to coating, paint, surface treatment agent, printing ink, or adhesive applications. The paraffins present in the composition can be produced by distillation from hydrotreated biological raw materials. The paraffins can be products of a process comprising hydrodeoxygenation and isomerization of biological raw materials.

According to an exemplary aspect, provided is a composition comprising C14 and C15 paraffins, said paraffins being produced from biological raw materials.

According to an exemplary aspect, provided is a method for producing said composition comprising C14 and C15 paraffins. The method can comprise hydrotreating a raw material of biological origin to obtain a hydrotreated product comprising n-paraffins and isomerizing the hydrotreated product to obtain an isomerized product comprising isoparaffins and separation of said composition by distillation.

As used herein, the term "biosolvent" refers to a solvent produced from biological raw materials. In an exemplary aspect, a composition is provided comprising C14 and C15 paraffins wherein only biological raw materials are used to form the C14 and C15 paraffins.

According to an exemplary aspect, the composition can comprise 40-50 wt-% C14 paraffins and 35-45 wt-% C15 paraffins, for example, 45-50 wt-% C14 paraffins and 40-45 wt-% C15 paraffins, for example, 48-50 wt-% C14 paraffins and 43-45 wt-% C15 paraffins, based on the total weight of the composition. As used herein, "C14 paraffin" refers to a paraffin containing 14 carbon atoms, and "C15 paraffin" refers to a paraffin containing 15 carbon atoms. The C14 and C15 paraffins are produced from a biological raw material.

In an exemplary embodiment, the composition can comprise less than 9 wt-% C13 and lighter paraffins and less than 7 wt-% C16 and heavier paraffins, based on the total weight of the composition. For example, the composition can comprise less than 5 wt-% C13 and lighter paraffins and less than 3 wt-% C16 and heavier paraffins, based on the total weight of the composition. For example, the composition can comprise less than 3 wt-% C13 and lighter paraffins and less than 1 wt-% C16 and heavier paraffins, based on the total weight of the composition.

In an exemplary embodiment, the total isoparaffinic content of the composition is more than 93 wt-%, based on the total weight of the composition. For example, the total isoparaffinic content of the composition is more than 97 wt-%, based on the total weight of the composition. For example, the total isoparaffinic content of the composition is more than 99 wt-%, based on the total weight of the composition.

In an exemplary embodiment, the composition can comprise 40-50 wt-% C14 isoparaffins and 35-45 wt-% C15 isoparaffins, for example, 45-50 wt-% C14 isoparaffins and 40-45 wt-% C15 isoparaffins, for example, 48-50 wt-% C14 isoparaffins and 43-45 wt-% C15 isoparaffins, based on the total weight of the composition. As used herein, "C14 isoparaffin" refers to a branched paraffin containing 14 carbon atoms, and "C15 isoparaffin" refers to a branched paraffin containing 15 carbon atoms.

In an exemplary embodiment, the total aromatic hydrocarbon content of the composition is less than 1500 ppm weight basis. For example, the total aromatic hydrocarbon content of the composition is less than 1300 ppm weight basis. For example, the total aromatic hydrocarbon content of the composition is less than 500 ppm weight basis.

In an exemplary embodiment, the C14 and C15 paraffins are produced by a process comprising hydrodeoxygenation and isomerization of a biological raw material.

In an exemplary embodiment, the composition has a boiling point in a range of 240° C. to 260° C., for example, in a range of 245° C. to 255° C., for example, in a range of 248° C. to 252° C.

In an exemplary embodiment, the composition is suitable for use as a solvent or a solvent component. In an exemplary embodiment, the composition is in liquid form.

In an exemplary embodiment, the composition is an emulsion. For example, the composition can be an oil-in-water emulsion or a water-in-oil emulsion. In an exemplary embodiment, the composition can be suitable for use in a coating, paint, lacquer, varnish, polish, ink, adhesive, sealant, resin, plastic, catalyst, cleaning composition, peroxide desensitizer, pigment dispersion, carrier fluid for an active ingredient, antioxidant, biocide, insecticide, air freshener, crop protection composition, detergent, grease removal composition, dry cleaning composition, cosmetic, personal care composition, pharmaceutical, extender in a dental impression material, vaccine, food ingredient, flavor composition, fragrance, natural oil extraction, oil field chemical, drilling mud composition, extraction process composition, plasticizer for elastomer, paper processing chemical, lubricant, functional fluid, transformer oil, metal working composition, rolling or cutting fluid, water treatment composition, wood treatment composition, construction chemical, mould release material, explosive, mining chemical, solvent extraction composition, fuel component, heating oil, lamp oil, or a combination thereof.

In an exemplary embodiment, a process for producing the composition is provided. The process includes conducting hydrodeoxygenation and isomerization processes of a biological raw material; and conducting a separation process of the resulting material, wherein the separation process includes distillation.

The present disclosure contains subject matter set forth in Kanokporn Sinthavarayan, "Fractionation and characterization of renewable paraffinic solvents," Thesis submitted in partial fulfillment of the requirements of the degree of Master of Science in Technology, Aalto University School of Chemical Technology, Environmental Pathways for Sustainable Energy Systems (SELECT) Master's Program, Espoo, Finland, Aug. 1, 2013 (hereinafter referred to as the "Aalto University Thesis," the entire contents of which are incorporated herein by reference.

Production of the n-Paraffins from Biological Materials

An exemplary composition is produced from starting materials of biological origin using, for example, a process first comprising a hydrodeoxygenation (HDO) step for decomposing the structure of the biological ester or triglyceride constituent, and for removing oxygen, phosphorus and sulfur compounds, concurrently hydrogenating the olefinic bonds, followed by isomerization of the product thus obtained, thus branching the hydrocarbon chain and improving the low temperature properties of the paraffin. The product is fractionated by distillation to give the desired fractions.

Biological raw materials from plants, animals or fish containing fatty acids and/or fatty acid esters may be used as the starting material. The raw material may be selected from vegetable oils, animal fats, fish oils, and mixtures thereof. Suitable biological raw materials include rapeseed oil, canola oil, colza oil, tall oil, sunflower oil, soybean oil, hemp oil, olive oil, linseed oil, mustard oil, palm oil, arachis oil, castor oil, coconut oil, animal fats such as suet, tallow, blubber, recycled alimentary fats, starting materials produced by genetic engineering, and biological starting materials produced by microbes such as algae and bacteria. Condensation products, esters, or other derivatives obtained from biological raw materials may also be used as starting materials.

In the HDO step, hydrogen gas and the biological constituent are passed to the HDO catalyst bed either in countercurrent or concurrent manner. In the HDO step, the pressure and the temperature range, for example, between 20 and 150 bar, and between 200 and 500 degrees centigrade, respectively. In the HDO step, any suitable hydrodeoxygenation catalysts may be used.

Prior to the HDO step, the biological raw material may optionally be subjected to prehydrogenation under milder conditions to reduce or avoid side reactions of the double bonds.

After the HDO step, the HDO product is passed to the isomerization step where hydrogen gas and the n-paraffin mixture are passed to the isomerization catalyst bed either concurrent or countercurrent manner to produce an isomerized product. The "steps" can be conducted in the same vessel or in separate vessels. The "steps" can occur in the same reaction zone or in different reaction zones.

In the isomerization step, the pressure and the temperature range, for example, between 20 and 150 bar, and between 200 and 500 degrees centigrade, respectively. In the isomerization step, any suitable isomerization catalysts may be used.

Solvent properties of the composition of an exemplary aspect are excellent, and thus it can be used as such or as components in, formulated into and as emulsions in coatings, paints, lacquers, varnishes, and in floor, metal or shoe polishes, and in inks, adhesives, sealants, resins and plastics production, including catalyst preparations and cleaning operations, peroxide desensitizer, pigment dispersion, carrier fluid for active ingredients such as antioxidants and biocides, insecticides, air fresheners, crop protection and alike, detergents, grease removal, dry cleaning, cosmetics, personal care, pharmaceuticals, extender in dental impression materials, vaccines, food ingredients, flavors, fragrances, natural oil extraction and alike, oil field chemicals, drilling muds and extraction processes and alike, plasticizer for elastomers, paper processing chemicals, lubricants, functional fluids, transformer oils, metal working and rolling and cutting fluids and alike, water treatment, wood treatment, construction chemicals, mould release materials, explosives and mining chemicals, solvent extraction, fuel components, heating and lamp oils.

Distillation of n-Paraffinic and Isoparaffinic Fractions

An exemplary composition is obtained by distillation of paraffins produced from biological raw materials. The paraffins can be produced by a method comprising hydrodeoxygenation of biological raw materials and optionally isomerization of the n-paraffinic mixture obtained from the hydrodeoxygenation.

The paraffinic fractions used in the following examples have been obtained by hydrotreatment of vegetable oils and isomerization of the produced n-paraffinic mixtures and by separation of the desired fractions by distillation.

The isoparaffinic mixture used in the following examples comprises largely isoalkanes with small amount of n-alkanes and naphthenes. Its major carbon chain length is, for example, between C6 and C18 and with ASTM D86 distillation range from 188 to 301° C. For example, the n-paraffinic mixture used in the examples consists primarily of n-alkanes with carbon distribution mainly from C12 to C22 and with TBP range from 216 to 319° C.

In an example, the four fractions of the isoparaffinic mixture have been obtained with pilot scale and laboratory scale distillation units. The heaviest fourth fraction obtained from pilot scale unit was further fractionated in laboratory scale fractionation unit to obtain two further fractions. The n-paraffinic mixture was only fractionated in laboratory scale unit to obtain three fractions. The distillation characteristics and unit operations used to obtain the isoparaffinic and n-paraffinic fractions are summarized in Table 1.

TABLE 1

Fractionation criteria

| Feedstock | Fractionation Unit | Criteria |
|---|---|---|
| Isoparaffinic mixture | Pilot scale | 1: IBP-200° C. |
| | | 2: 200-230° C. |
| | | 3: 230-260° C. |
| | | 4: 260° C. -FBP |
| Fraction 4 (260° C. - FBP) | Laboratory scale (Test Equipment 1) | 1: 260-285° C. |
| | | 2: 285° C. -FBP |
| N-paraffinic mixture | Laboratory scale (Test Equipment 2) | 1: C16 and lighter components |
| | | 2: C16-C18 |
| | | 3: C18 and heavier components (aiming for 90 wt. % C18) |

Pilot scale fractionation was conducted in a continuous distillation unit comprising 3 multistage columns. The first column separates the lightest fraction and the bottom fraction was sent to the second column to distillate the second fraction from the feed. Then, the bottom from second column was sent to the third column for final fractionation. The first two columns were operated at atmospheric pressure while the third column was operated in vacuum.

Two laboratory scale fractionation units named "Test Equipment 1" and "Test Equipment 2" were used for isoparaffinic and normal paraffinic mixtures fractionation, respectively. The principle of these units is batch multi-stage distillation operated in vacuum pressure.

Fractions obtained from fractionation were analyzed for their physical properties, composition and also preliminary evaluation for their applications. The standard methods and methodology used are described in the sections below.

Applicability Evaluation

Materials and chemicals used for applicability evaluation are presented in Table 2 below.

TABLE 2

List of materials used in the experiments.

| Type | Description | Source |
|---|---|---|
| Pigment | Carbon black FW 200 | Orion Engineered Carbons |
| Pigment | Titanium dioxide Sachtleben R660 (min. 93% $TiO_2$ content) | Sachtleben |
| Liquid | WACKER ® AK 1000 (Silicone Fluid) | WACKER SILICONES |
| Liquid | EPIKOTE ™ Resin 828 (Epoxy resin) | MOMENTIVE |
| Liquid | FlexiSolv ™ DBE ® Esters (min. 99.5 wt. % Ester content) | INVISTA Specialty Materials |
| Liquid | SYLFAT ® 2 (tall oil fatty acid with typically 96% free fatty acids) | Arizona CHEMICAL |
| Liquid | Rapeseed Oil | Neste Oil Corporation |
| Emulsifier | Berol 791 | AkzoNobel |
| Emulsifier | SIMULSOL ™ 165 (glycerol monostearate) | SEPPIC |
| Emulsifier | MULSIFAN CB (100% mixture of fatty alcohol polyglycol ethers) | ZSCHIMMER & SCHWARZ |
| Plastic/ elastomer | VINNAPAS UW 10 FS (poly vinyl acetate) | WACKER POLYMERS |
| Plastic/ elastomer | Radilon S (polyamide 6) | RadiciGroup Plastics |
| Plastic/ elastomer | Radilon A (polyamide 66) | RadiciGroup Plastics |
| Plastic/ elastomer | Radilon D (polyamide 610) | RadiciGroup Plastics |
| Plastic/ elastomer | KRATON ® G1650 Polymer: Styrene-Ethylene/Butylene-Styrene (SEBS) | Kraton Polymers |
| Plastic/ elastomer | KRATON ® G1654 Polymer: Styrene-Ethylene/Butylene-Styrene (SEBS) | Kraton Polymers |
| Plastic/ elastomer | KRATON ® FG1901 Polymer: Maleated Styrene-Ethylene/Butylene-Styrene (SEBS) | Kraton Polymers |
| Plastic/ elastomer | KRATON ® D1102 Styrene-Butadiene-Styrene (SBS) Polymer | Kraton Polymers |
| Plastic/ elastomer | Copolymer from butadiene and acrylonitrile, nitrile rubber (NBR) | Etola |
| Plastic/ elastomer | Polychloroprene (CR) | Etola |
| Plastic/ elastomer | Elastomeric terpolymer from ethylene, propylene and a nonconjugated diene (EPDM) | Etola |
| Plastic/ elastomer | Silicone rubber (SIL) | Etola |
| Plastic/ elastomer | Natural rubber (NR) PARA | Etola |
| Plastic/ elastomer | Natural rubber (NR) NAT 1729 | Etola |
| Plastic/ elastomer | Thermoplastic polyurethanes tube- blue (TPU) | Etola |
| Plastic/ elastomer | Thermoplastic polyurethanes tube - colorless (TPU) | Etola |
| Plastic/ elastomer | Polyurethane (PUR) | Etola |
| Plastic/ elastomer | Polyamide 10 tube (PA 610) | Etola |
| Plastic/ elastomer | Polycarbonate (PC) | Etola |

TABLE 2-continued

List of materials used in the experiments.

| Type | Description | Source |
|---|---|---|
| Plastic/elastomer | Polyvinylchloride tube (PVC) | Etola |
| Plastic/elastomer | Polyethylene terephthalate (PET) | PET bottle |
| Plastic/elastomer | Polystyrene (PS) | Pencil sharpener case |
| Plastic/elastomer | Polypropylene (PP) | Highlighter pen cap |
| Plastic/elastomer | Polyethylene (PE) | Etola |
| Plastic/elastomer | Polymethylmethacrylate (PMMA) | Etola |
| Commercial Solvent | ShellSol T | Shell Chemicals |
| Commercial Solvent | ShellSol A 100 | Shell Chemicals |

Physical Properties

All nine fractions obtained in fractionation were analyzed for their physical properties. List of physical properties and the standard methods used are shown Table 3 below.

Apart from the fractions in Table 2, fractions with boiling range 190-220° C. and 220-240° C. obtained from laboratory scale isoparaffinic mixtures fractionation and the fractions obtained from 40% and 95% distillation program by ASTM D86 apparatus were analyzed for their surface tensions, electrical conductivities, colours and bromine indexes. These additional analyses were done for comparison and consistency checking with obtained isoparaffinic fractions.

TABLE 3

List of physical properties examined for the samples.

| No. | Description | Method | Note | Reference |
|---|---|---|---|---|
| 1 | Distillation | ASTM D86, ASTM D7345, ASTM D2887 | The method is chosen depending on the available amount of sample and ASTM D2887 is used when TBP curve is required. | [Cited Document 15], [Cited Document 13], [Cited Document 20] |
| 2 | Flash Point | ASTM D93, ASTM D56 | ASTM D93 covers the valid range from 40 to 360° C. and ASTM D56 is valid for the liquids with a viscosity below 5.5 mm$^2$/s at 40° C. or below 9.5 mm$^2$/s at 25° C. and a flash point below 93° C. | [Cited Document 80], [Cited Document 81] |
| 3 | Aniline Point | ASTM D611 | — | [Cited Document 82] |
| 4 | Kinematic Viscosity | ASTM D445 | — | [Cited Document 48] |
| 5 | Viscosity index | ASTMD2270 | The practice does not apply to products with kinematic viscosities less than 2.0 mm$^2$/s at 100° C. | [Cited Document 49] |
| 6 | Density | ASTM D4052 | — | [Cited Document 83] |
| 7 | Surface Tension | ASTMD971 | The method is modified for surface tension determination by Neste Oil. | — |
| 8 | Electrical conductivity | ASTMD2624 | — | [Cited Document 85] |
| 9 | Kauri-Butanol number | ASTM D1133 | — | — |
| 10 | Pour point | ASTMD5950 | This test method covers the range of temperatures from −57 to +51° C. | [Cited Document 43] |
| 11 | Cloud point | ASTMD5771 | This test method covers the range of temperatures from −60 to +49° C. | [Cited Document 44] |
| 12 | Relative evaporation rate of solvents to diethyether | DIN 53170 | The valid range of this method is from 1 to 600. The test is done at 30% relative humidity instead of 50% relative humidity as stated in the method. | — |
| 13 | Saybolt Color | ASTMD6045 | The scale is range from −16 (darkest) to +30 (lightest). | [Cited Document 88] |
| 14 | Refractive index | ASTMD1218 | — | [Cited Document 89] |
| 15 | Vapor Pressure | Calculated | Calculated from VP Tool | — |
| 16 | Solubility parameter | Estimated | Estimated by extrapolation from solubility parameter and Kauri-butanol number relation in from 6. | — |

Composition Analysis

The purpose of composition analysis is to determine the carbon distribution and structure of the fractions, including the analysis for specific component which are unsaturated hydrocarbon, aromatic, sulphur and benzene content were analyzed.

Carbon Number and Structure Analysis

Carbon number and structure analysis was done by gas chromatography equipped with Flame Ionization Detector (FID) method. The method is used to determine n-paraffins and paraffin isomers in the sample. It is valid for analyzing within the carbon number ranges from C6 to C36 and the limit of quantification for individual components is 0.01 wt. %.

Moreover, paraffins, isoparaffins, olefins, naphthenes and aromatics (PIONA) analysis was also conducted to determine hydrocarbon component and group type. This method utilizes gas chromatography with FID to determine the paraffins, isoparaffins, olefins, naphthenes and aromatics. It also gives the concentration of each hydrocarbon in the sample. The method is valid for light oils with boiling point less than 250° C., therefore only the first fraction of isoparaffinic mixture with boiling point range from IBP to 200° C. was analyzed.

Bromine Index

Bromine index determination was conducted according to ASTM D2710 ([Cited Document 92]) and modified ASTM D2710. It is a method to measure trace amounts of unsaturates in sample in term of Bromine index. Bromine index is the number of milligrams of bromine that will react with 100 grams of sample. The principle of this method is that a known mass of the sample, dissolved in a specified solvent, is titrated with standard bromide-bromate solution. The end point is indicated by electrometric titration apparatus when the presence of free bromide causes a sudden change in the electrical conductivity of the system. It is applicable to sample having bromine indexes below 1000.

Aromatic Content

A test was used for aromatic content determination in which the absorbance of the aromatic hydrocarbon is measured at known wavelengths by Ultraviolet (UV)-spectrophotometer to define the aromatic content.

Sulphur Content

ASTM D5453 was used to determine the total sulphur content in the sample ([Cited Document 95]). The tests were done by Central Laboratory, Neste Oil Corporation. The sample is injected into a high temperature combustion tube where the sulphur is oxidized to sulphur dioxide in oxygen rich atmosphere. Then, sulphur dioxide absorbs the energy from UV light and is converted to its excited state. The sulphur content is determined by measuring the fluorescence emitted from the sulphur dioxide with a photomultiplier tube.

Benzene Content

Trace amount of benzene is measured by gas chromatography with mass spectrometry.

Preliminary Applicability Evaluation

The preliminary applicability evaluation comprises three parts which are chemical compatibility, ability to form emulsion and pigment dispersion stability. Due to limitation of sample amount, only 4 fractions from pilot scale fractionation were tested for applicability evaluations described below.

Chemical Compatibility

The compatibility between fractions and test materials both in liquid or solid states were evaluated by the method based on the experiments described by C. Chiyoda et al. ([Cited Document 97]) and C. Bordes et al. ([Cited Document 54]).

For liquid test materials, 10 mL of fraction sample and 10 mL of liquid test material were mixed and stirred with magnetic stirrer for 20 min. Then, the mixture was let to stand for 24 h. and then visual inspections of the solubility result were conducted. In addition, testing temperature was increased to 50° C. and 80° C. in case the test material was partial soluble or insoluble.

For solid test materials, 15 mL of fraction sample was mixed with 1.5 g of test material and stirred with a magnetic stirrer for 1 hour. The mixture was let to stand for 24 h. and then visual inspections of the solubility result were done. In addition, the changing in weight of solid materials was measured if applicable. The percentage of weight change was calculated using equation (1). Testing temperature was increased to 50° C. and 80° C. in case of partial dissolved or non-dissolved test material.

$$\text{weight change } (\%) = \frac{(W_f - W_i)}{W_i} \times 100 \qquad (1)$$

Where $W_f$ is the weight of the test material after mixing $W_i$ is the weight of the test material before mixing Due to high resistance for polyamide, Radilon materials were tested for swelling. This test method is based on the experiments described by S. J. Kim et al. ([Cited Document 62]), chemical compatibility test kit by ALZAID ([Cited Document 98]) and solvent resistance report done by ARKEMA ([Cited Document 99]). The polymer beads were weighted for 1.5 g. and immersed in fraction sample. Then, the mixture was kept in the oven at 60° C. After 8 days, the polymer beads were blot dry and weighted and the gravimetric swelling ratio was calculated applying equation (1). Compatibility tests with ShellSol T which is isoparaffinic solvent and ShellSol A 100 which is aromatic solvent were performed for comparison.

For preliminary chemical compatibility classification, the scale in Table 4 was used. The scale is based the Plastics Design Library (PDL) resistance rating ([Cited Document 55]) shown in Table 5. The accuracy of the laboratory weight scale at 0.01 g or 0.67% of the original weight of sample was also taken into account. The purpose of using this scale is for easily visual determining the level of the compatibility. Moreover, since the test temperature cannot be higher than the flash point of sample, some tests at elevated temperature were skipped, for example fraction with boiling range IBP-200° C. was tested at room temperature only.

TABLE 4

| Chemical compatibility scale | |
|---|---|
| Weight change (%) | Description |
| 0 to 0.75 | No or minor change |
| 0.75 to 2.5 | Slightly dissolve or swelling |
| 2.5 to 5 | Dissolve or swelling |
| >5 | Significant dissolve or swelling |

TABLE 5

Plastic Design Library (PDL) resistance rating

| Weighted Value | Weight Change* | Diameter; Length Change* | Volume Change* | Mechanical Property Retained** | Visual/Observed Change*** |
|---|---|---|---|---|---|
| 10 | 0-0.25 | 0-0.1 | 0-2.5 | >=97 | No change |
| 9 | >0.25-0.5 | >0.1-0.2 | >2.5-5.0 | 94-<97 | |
| 8 | >0.5-0.75 | >0.2-0.3 | >5.0-10.0 | 90-<94 | |
| 7 | >0.75-1.0 | >0.3-0.4 | >10.0-20.0 | 85-<90 | Slightly discolored, slightly bleached |
| 6 | >1.0-1.5 | >0.4-0.5 | >20.0-30.0 | 80-<85 | discolored yellows, slightly flexible |
| 5 | >1.5-2.0 | >0.5-0.75 | >30.0-40.0 | 75-<80 | Possible stress crack agent, flexible, possible oxidizing agent, slightly crazed |
| 4 | >2.0-3.0 | >0.75-1.0 | >40.0-50.0 | 70-<75 | Distorted, warped, softened, slight swelling, blistered, known stress crack agent |
| 3 | >3.0-4.0 | >1.0-1.5 | >50.0-70.0 | 60-<70 | Cracking, crazing, brittle, plasticizer oxidizer, softened swelling, surface hardened |
| 2 | >4.0-6.0 | >1.5-2.0 | >60.9-90.0 | 50-<60 | Severe distortion, oxidizer and plasticizer deteriorated |
| 1 | >6.0 | >2.0 | >90.0 | >0-<50 | decomposed |
| | | | | 0 | solvent dissolved, disintegrated |

*All values are given as percentage change from original.
**Percentage mechanical properties retained include tensile strength, elongation, modulus, flexible strength and impact strength. If the % retention is greater than 100%, a value of 200 minus the % property retained is used in the calculations.
***Due to the variety of information of this type reported, this information can be used only as a guideline.

Ability to Form Emulsion

To evaluate the ability to form emulsion between sample and water with the presence of emulsifier, the method is based on the ASTM D1401 standard test method for water separability of Petroleum Oils and Synthetic fluids ([Cited Document 100]), the experiment done by Daaou and Bendedouch ([Cited Document 101]) and technical data sheets from emulsifiers' manufacturers ([Cited Document 102], [Cited Document 103], [Cited Document 104]). In addition, the tests without surfactant were conducted as a base line. Both W/O and O/W emulsions were prepared by changing the phase for melting emulsifier and order of addition ([Cited Document 105]). Table 5 summarizes the emulsion preparation for each emulsifier. For W/O emulsion, the tests were skipped for fractions which have their flash point lower than the melting temperature of emulsifier. Then, the mixtures were stirred at the speed of 1500±15 rpm for 5 min.

For each emulsion, monitoring the emulsion stability was done every 10 min for the first hour and then every 1 hour interval for another 5 hours. The sample was then left to stand for 24 hr. at room temperature (23° C.) for observation. If the emulsion was still stable, the sample then was put in the refrigerator at 4° C. for 24 hr. and further subjected to Freeze/Thaw cycle until the emulsion was broken. Many ASTM standards for freeze/thaw resistance are available for different applications for example ASTM D5678 for wax emulsion floor polish, ASTM D3209 for polymer floor polishes, ASTM D2243 for water-borne coatings and ASTM D7149 for adhesives ([Cited Document 106]). However, the Freeze/Thaw cycle test is simplified in this preliminary evaluation. Therefore, one cycle was that the emulsion was kept in freezer around −14° C. for 24 hr. and then it was left to thaw for 24 hr. at room temperature. The time when the emulsion breaking occurred was recorded and the volume of oil phase, water phase and emulsion layer were measured.

TABLE 6

Summary of emulsion preparation.

| Emulsifier | Type | Mixing step | Temp. (° C.) |
|---|---|---|---|
| None | — | 40 mL water + 40 mL oil | 23 |
| Berol 791 | W/O | 40 mL water → 40 mL oil + emulsifier (3 vol. %) | 23 |
| | O/W | 40 mL oil → 40 mL water + emulsifier (3 vol. %) | 23 |
| SIMULSOL 165 | W/O | 40 mL water → 40 mL oil + emulsifier (5 wt. %) | 75 |
| | O/W | 40 mL oil → 40 mL water + emulsifier (5 wt. %) | 75 |
| MULSIFAN CB | W/O | 40 mL water → 40 mL oil + emulsifier (5 wt. %) | 65 |
| | O/W | 40 mL oil → 40 mL water + emulsifier (5 wt. %) | 65 |

Pigment Dispersion Stability

The method for evaluating pigment dispersion stability is based on the experiment done by Q. Li et al. ([Cited Document 68]). The 15 mL of sample was mixed with 0.2 g. of the pigment with magnetic stirrer for 30 min. The sedimentation behavior was monitored at 10 min., 30 min., 1 h., 1.5 h. and 24 h. In addition, stability tests with water, acetone, xylene and aromatic free paraffinic solvent were conducted for comparison. A qualitative scale in Table 6 was used to categorize the pigment dispersion stability level.

TABLE 7

Scale used to assess the stability of the suspensions. [68]

| Characteristics[a] | Settling time[b] (hour) | Stability scale |
|---|---|---|
| clear | <1.5 | Unstable |
| Slightly cloudy | <1.5 | Moderately stable |
| Cloudy | 1.5-24 | stable |
| Cloudy | >24 | Very stable |

[a]At 1.5 h
[b]To reach sediment volume equal to 20% of the initial volume.

Example 1

Fractionation Yields

The yields of each fraction from isoparaffinic mixture fractionation are presented in Table 8 based on both mass and volume basis.

In case that the complete fractionation into 5 fractions was considered, their yields were calculated and also shown in Table 8. As can be seen, the major fractions are fraction 285-FBP and fraction 260-285 with the yield of 49 wt. % and 33 wt. %, respectively, being significantly higher than the yields of other 3 fractions.

TABLE 8

Yield of isoparaffinic mixture fractionation.

| Fractionation unit | Fraction | Separate fractionation Yield (wt. %) | Separate fractionation Yield (vol. %) | Complete fractionation Yield (wt. %) | Complete fractionation Yield (vol. %) |
|---|---|---|---|---|---|
| Pilot scale | 1: IBP-200 | 7.32 | 7.69 | 7.32 | 7.69 |
|  | 2: 200-230 | 5.46 | 5.60 | 5.46 | 5.60 |
|  | 3: 230-260 | 4.90 | 4.96 | 4.90 | 4.96 |
|  | 4: 260-FBP | 82.32 | 81.75 | — | — |
|  | Total | 100.00 | 100.00 | — | — |
| Laboratory scale | 1: 260-285 | 39.93 | 40.13 | 32.87 | 32.81 |
|  | 2: 285-FBP | 60.07 | 59.87 | 49.44 | 48.94 |
|  | Total | 100.00 | 100.00 | — | — |
|  | Grand total | — | — | 100.00 | 100.00 |

The Laboratory distillations were done for each fraction as show in Table 9. It can be seen that the obtained fractions are within the boiling point limits of the fractions except for the IBP of 230-260 fraction which is lower than the criteria by roughly 6° C.

TABLE 9

Laboratory distillation results for isoparaffinic fractions.

| | IBP-200 | 200-230 | 230-260 | 260-FBP | 260-285 | 285-FBP |
|---|---|---|---|---|---|---|
| Method | D86 | D86 | D86 | D86 | D7345 | D7345 |
| IBP | 131.6 | 198.5 | 223.9 | 266.8 | 262.7 | 288.9 |
| 5% | 153.2 | 208.4 | 231.8 | 276.7 | 264.8 | 292.1 |
| 10% | 158.0 | 209.6 | 232.3 | 277.4 | 267.0 | 294.0 |
| 20% | 164.4 | 211.5 | 233.6 | 278.5 | 267.4 | 294.4 |
| 30% | 169.4 | 213.0 | 234.7 | 279.7 | 267.6 | 294.6 |
| 40% | 173.6 | 214.3 | 235.8 | 281.0 | 268.0 | 294.9 |
| 50% | 176.4 | 215.5 | 237.0 | 282.4 | 268.4 | 295.3 |
| 60% | 179.4 | 216.7 | 238.2 | 284.0 | 268.9 | 295.6 |
| 70% | 182.5 | 218.1 | 239.7 | 285.9 | 269.8 | 296.0 |
| 80% | 185.4 | 219.7 | 241.6 | 288.4 | 271.4 | 296.6 |
| 90% | 189.1 | 222.2 | 244.4 | 292.0 | 273.8 | 297.9 |
| 95% | 191.8 | 224.6 | 247.4 | 295.5 | 275.9 | 299.6 |
| FBP | 195.5 | 228.7 | 252.9 | 300.1 | 278.2 | 306.8 |

The yields of each fraction from n-paraffinic mixture fractionation are presented in Table 10 based on both mass and volume basis. The yield of the fractions are roughly 16, 38 and 46 wt. % for first, second and third fraction, respectively. In addition, the carbon number distribution of each fraction is shown in Table 11. The components of each fraction show that the fractions met the criteria defined by the name of the fraction. The purity of C18 in the fraction of C18 and heavier components is 86.2 wt. % which is slightly less that the aimed target at 90 wt. %. In this fraction, the heavier components account for 7.5 wt. %, while the lighter components represent around 6.3 wt. % and the C18 recovery of this focused fraction is at 76 wt. % of the C18 present in the feedstock.

TABLE 10

Yield of n-paraffinic mixture fractionation

| Fraction | Yield (wt. %) | Yield (vol. %) |
|---|---|---|
| 1: C16 and lighter components | 16.27 | 16.49 |
| 2: C16-C18 | 38.06 | 38.12 |
| 3: C18 and heavier components | 45.67 | 45.39 |
| Total | 100.00 | 100.00 |

TABLE 11

Carbon number distribution of n-paraffinic fraction

| Carbon no. | C16 and lighter component | C16-C18 | C18 and heavier component |
|---|---|---|---|
| 7 | 0.06 | 0.00 | 0.00 |
| 8 | 0.30 | 0.00 | 0.00 |
| 9 | 0.42 | 0.00 | 0.00 |
| 10 | 0.71 | 0.00 | 0.00 |
| 11 | 0.58 | 0.00 | 0.00 |
| 12 | 1.32 | 0.00 | 0.00 |
| 13 | 3.67 | 0.00 | 0.00 |
| 14 | 12.23 | 0.01 | 0.00 |
| 15 | 38.14 | 2.20 | 0.00 |
| 16 | 38.61 | 34.20 | 0.12 |
| 17 | 3.26 | 31.39 | 6.15 |
| 18 | 0.68 | 31.91 | 86.21 |
| 19 | 0.03 | 0.21 | 2.07 |
| 20 | 0.00 | 0.07 | 3.33 |
| 21 | 0.00 | 0.01 | 0.40 |
| 22 | 0.00 | 0.00 | 0.65 |
| 23 | 0.00 | 0.00 | 0.11 |
| 24 | 0.00 | 0.00 | 0.09 |
| 25 | 0.00 | 0.00 | 0.00 |
| >C36 | 0.00 | 0.00 | 0.02 |
| C25-C29 | 0.00 | 0.00 | 0.61 |
| C30-C36 | 0.00 | 0.00 | 0.24 |
| Total | 100.00 | 100.00 | 100.00 |

Both fractionations met the set criteria. For isoparaffinic mixture fractionation, main fractions obtained are the fractions with boiling range of 285° C.-FBP and 265-285° C.

with the yields of 49 and 33 wt. % respectively. The major fraction from n-paraffinic mixture is the C18 and heavier component fraction with yield of 46 wt. %. This fraction contains around 86 wt. % of C18 and 76% of C18 recovery into this fraction was achieved. Although the C18 purity in this main fraction is slightly less than the aimed target, it can be possible to achieve the target in industrial scale distillation.

Example 2

Physical Properties of the Fractions

Table 12 below shows the physical properties of isoparaffinic fractions. The properties that are increasing with higher boiling range are flash point, aniline point, kinematic viscosity, density, surface tension, pour point, cloud point, relative evaporation rate and refractive index. On the other hand, the properties that decreasing with increasing boiling range are Kauri-butanol solubility test, solubility parameter and vapor pressure.

The pour point of all boiling ranges is lower than −55° C. and the cloud point varies from −23° C. to lower than −60° C. The relative evaporation rates are 46 and 233 for the two lightest fractions respectively, while they increase significantly to be higher than the upper limit of the test for the heavier fractions. The vapor pressure calculation shows than the fractions with boiling range of IBP-200° C. and 200-230° C. are classified as VOCs, while other heavier ones are non-VOCs. The refractive index slightly increases from 1.415 to 1.439 as a function of increasing boiling range.

As an indication of the dissolving power, KB ranges from 18.5 to 26 and the solubility parameters are estimated based on KB test varying from 13.9 to 14.5 $(MJ/m3)^{1/2}$. The detailed calculations are shown in Appendix F.1 of Kanokporn Sinthavarayan, "Fractionation and characterization of renewable paraffinic solvents," Thesis submitted in partial fulfillment of the requirements of the degree of Master of Science in Technology, Aalto University School of Chemical Technology, Environmental Pathways for Sustainable

TABLE 12

Physical properties of isoparaffinic fractions

| No. | Physical Properties | unit | Iso-paraffinic feedstock | Pilot scale (IBP-200) | Pilot scale (200-230) | Pilot scale (230-260) | Pilot scale (260-FBP) | Test Equipment 1 (260-285) | Test Equipment 1 (285-FBP) |
|---|---|---|---|---|---|---|---|---|---|
| 1 | IBP | ° C. | 188.2 | 131.6 | 198.5 | 223.9 | 266.8 | 262.7 | 288.9 |
|   | FBP | ° C. | 300.9 | 195.5 | 228.7 | 252.9 | 300.1 | 278.2 | 306.8 |
| 2 | Flash Point | ° C. | 78.5 | 32.0 | 77.0 | 97.0 | 133.0 | 125.0 | 145.0 |
| 3 | Aniline Point | ° C. | 95.6 | 79.2 | 85.9 | 89.9 | 97.9 | 95.3 | 99.5 |
| 4 | Kinematic Viscosity @ 20° C. | $mm^2/s$ | 4.198 | 1.23 | 2.09 | 2.857 | 5.270 | 4.222 | 6.002 |
|   | Kinematic Viscosity @ 40° C. | $mm^2/s$ | 2.712 | <1 | 1.521 | 1.950 | 3.291 | 2.785 | 3.682 |
|   | Kinematic Viscosity @ 100° C. | $mm^2/s$ | — | <1 | <1 | <1 | 1.306 | 1.157 | 1.416 |
| 5 | Viscosity index | — | — | N/A | N/A | N/A | N/A | N/A | N/A |
| 6 | Density @ 15° C. | $kg/m^3$ | 778.0 | 740.3 | 760.4 | 769.5 | 783.4 | 779.5 | 786.1 |
|   | Density @ 20° C. | $kg/m^3$ | — | 736.5 | 756.9 | 766.0 | 780.1 | 776.1 | 782.7 |
|   | Density @ 50° C | $kg/m^3$ | — | — | — | — | — | — | — |
| 7 | Surface Tension @ 23° C. | mN/m | 27.3 | 24.3 | 25.9 | 26.5 | 27.8 | 25.4 | 24.9 |
| 8 | Electrical conductivity@ 23° C. | pS/m | 2 | <1 | <1 | <1 | 6 | <1 | 11 |
| 9 | Kauri-Butanol Solubility test | — | — | 26 | 23.5 | 22.5 | 19.5 | 20 | 18.5 |
| 10 | Pour point | ° C. | — | <−57 | <−57 | <−57 | −56 | <−57 | −55 |
| 11 | Cloud point | ° C. | −34 | <−60 | <−60 | <−60 | −28 | −47 | −23 |
| 12 | Relative evaporation rate of solvents to diethyether | — | — | 46 | 233 | >600 | >600 | >600 | >600 |
| 13 | Color | Saybolt | 28 | +30 | +30 | +30 | 22 | +30 | 17 |
| 16 | Vapor Pressure | kPa | 0.003 | 0.195 | 0.019 | 0.006 | 0.000 | 0.001 | 0.000 |
| 17 | Refractive index @ 20° C. | — | — | 1.4147 | 1.4253 | 1.4300 | 1.4375 | 1.4351 | 1.4387 |
| 20 | Solubility parameter | $(MJ/m^3)^{1/2}$ | — | 14.5 | 14.3 | 14.2 | 14.0 | 14.0 | 13.9 |

Flash point is ranging from 32° C. for lightest fraction to 145° C. for heaviest fraction. Aniline point also increases from 79.2° C. to 99.5° C. as a function of the boiling ranges. Kinematic viscosity varies from less than 1 to 6 $mm^2/s$ depending on the boiling range. The lower temperature leads to higher in viscosity. However, the viscosity index cannot be calculated, since the viscosity at 100° C. is less than 2 for all the fractions and it is in the invalid range of the standard. The density of the samples varies from 740 to 786 $kg/m^3$.

Figure 2:
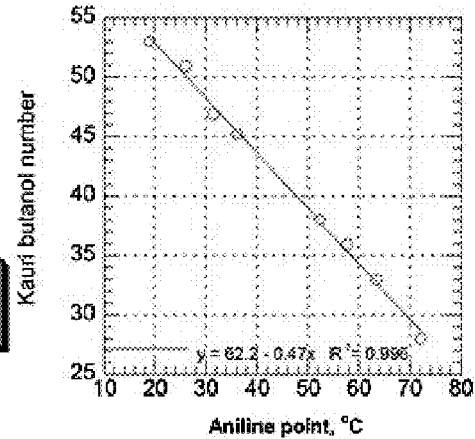
FIG. 2 depicts a graph of Kauri butanol number vs. aniline point, according to an exemplary aspect.
Figure 3:
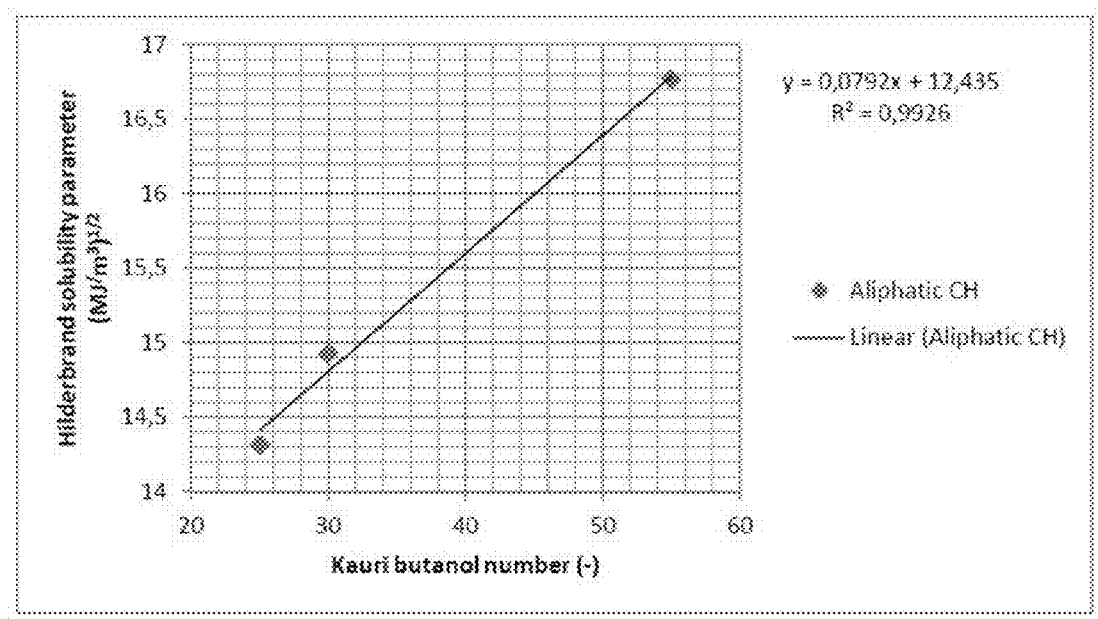
FIG. 3 depicts a graph of a correlation between Kauri-butanol number and solubility parameter, according to an exemplary aspect.

Energy Systems (SELECT) Master's Program, Espoo, Finland, Aug. 1, 2013 (hereinafter referred to as the "Aalto University Thesis," the entire contents of which are incorporated herein by reference. Specifically, the solubility parameters are estimated from the relation between KB and solubility parameter shown in FIG. 1 (Kauri butanol number vs. Hidebrand solubility parameter) and FIG. 2 (Kauri butanol number vs. aniline point) ([Cited Document 40]) (FIG. 14 of the Aalto University Thesis). The estimated trend line shown in FIG. 3 (correlation between Kauri-butanol number and solubility parameter) is used in extrapolating the solubility parameter.

dissolving powers are significantly lower than the aromatic solvents, e.g., toluene or benzene which have KB:s of 112 and 105, respectively.

TABLE A.1

General physical properties of n-paraffinic and isoparaffinic solvents

| Physical Property | Unit | Heptane | Octane | 2-Methyl hexane | 2,4-Dimethyl pentane | 2,2,3-Trimethyl pentane | 2,2,4-Trimethyl pentane |
|---|---|---|---|---|---|---|---|
| Chemical Structure | | Alkane | Alkane | Isoalkane | Isoalkane | Isoalkane | Isoalkane |
| Chemical formula | | $C_7H_{18}$ | $C_8H_{18}$ | $C_7H_{16}$ | $C_7H_{16}$ | $C_8H_{18}$ | $C_8H_{18}$ |
| Molecular weight | g/mol | 100 | 114 | 100 | 100 | 114 | 114 |
| Boiling point | ° C. | 98 | 126 | 90 | 81 | 110 | 100 |
| Freezing point | ° C. | −30 | −57 | −118 | −119 | −112 | −107 |
| Density @ 20° C. | kg/m$^3$ | 683.8 | 702.7 | 678.6 | 672.7 | 716.0 | 691.9 |
| Refractive index @ 20° C. | — | 1.3876 | 1.3974 | 1.3849 | 1.3815 | 1.4030 | 1.3915 |
| Viscosity @20° C. | mm$^2$/s | 0.611 | 0.778 | 0.557 | 0.535 | 0.835 | 0.728 |
| Surface tension: @ 25° C. | mN/m | 19.70 | 21.18 | 18.80 | 17.66 | 20.22 | 18.32 |
| Electrical conductivity | pS/m | <0.01 | — | — | — | — | — |
| Solubility parameter @ 25° C. | (MJ/m$^3$)$^{1/2}$ | 15.20 | 15.48 | 14.80 | 14.24 | 14.70 | 14.01 |
| Flash point | ° C. | −1 | 22 | — | −12 | — | −12 |
| Relative evaporation (ether = 1) | — | 3 | — | — | — | — | — |
| Kauri-Butanol value | — | 31 | — | — | — | — | 27 |
| Reference | | [41-42] | [42] | [42] | [42] | [42] | [41-42] |

TABLE A.2

General physical properties of aromatic and naphthenic solvents

| Physical Property | Unit | Benzene | Toluene | Methyl cyclopentane | Cyclohexane | Methyl cyclohexane | Ethyl cyclohexane |
|---|---|---|---|---|---|---|---|
| Chemical Structure | | Aromatic | Aromatic | Naphthene | Naphthene | Naphthene | Naphthene |
| Chemical formula | | $C_6H_6$ | $C_7H_8$ | $C_6H_{12}$ | $C_6H_{12}$ | $C_7H_{14}$ | $C_8H_{16}$ |
| Molecular weight | g/mol | 78 | 92 | 84 | 84 | 98 | 112 |
| Boiling point | ° C. | 80 | 111 | 71 | 81 | 101 | 132 |
| Freezing point | ° C. | 6 | −95 | −142 | 6.72 | −127 | −111 |
| Density @ 20° C. | kg/m$^3$ | 879.0 | 866.8 | 748.6 | 778.6 | 769.4 | 787.9 |
| Refractive index @ 20° C. | — | 1.5011 | 1.4969 | 1.4097 | 1.4262 | 1.4231 | 1.4330 |
| Viscosity @20° C. | mm$^2$/s | 0.738 | 0.676 | 0.677 | 1.252 | 0.954 | 1.070 |
| Surface tension @ 25° C. | mN/m | 28.20 | 27.92 | 21.72 | 24.65 | 23.29 | 25.14 |
| Electrical conductivity | pS/m | 0.004 | 0.08 | — | 0.0007 | <0.01 | — |
| Solubility parameter @ 25° C. | (MJ/m$^3$)$^{1/2}$ | 18.74 | 18.23 | — | 16.78 | 15.99 | 16.30 |
| Flash point | ° C. | −11 | 4 | −27 | −17 | −6 | 22 |
| Relative evaporation (ether = 1) | — | 2.6 | 6.1 | — | — | — | — |
| Kauri-Butanol value | — | 112 | 105 | — | — | — | — |
| Reference | | [41-42] | [41-42] | [42] | [42] | [42] | [42] |

Figure 6:
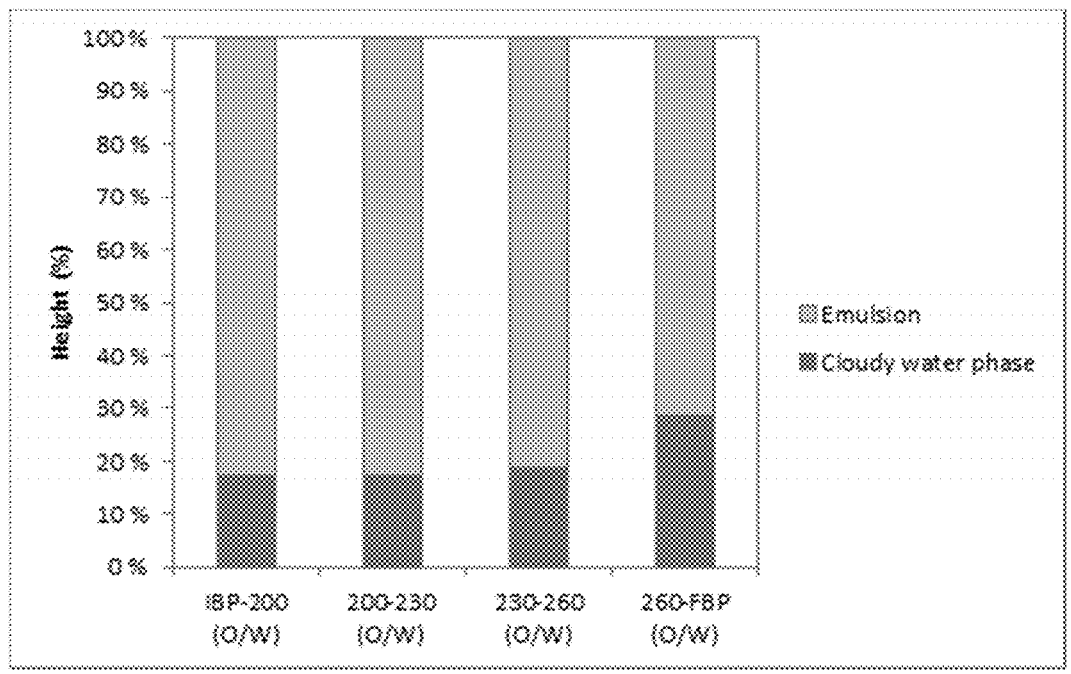
FIG. 6 depicts a graph in connection with different layers in O/W emulsions with Berol 791 after 24 hours at 23° C., according to an exemplary aspect.

The Kauri-butanol value (KB) is the amount of solvent, which is required to reach the cloud point used, for titrating a standard Kauri resin solution in 1-butanol. While, Aniline point (AP) is a maximum temperature at which the aniline and tested solvent liquids are separate into two phases. AP can be correlated with KB and also the solubility parameter as shown in FIG. 6. Even though, these values cannot be used for the solvent selection to a given pair of solvent-solute as the solubility parameters. They can provide some suggestions which solvents can be used in selected industries such as in paints and coatings ([Cited Document 39]).

The lighter fractions show more dissolving power than heavier fractions. Comparing with typical physical properties of other solvents in the following Tables A.1 and A.2 (and Appendix A of the Aalto University Thesis), KB of these fractions is lower than KB of 2,2,4 trimethylpentane being 27 and n-hexane with KB of 31. In addition, the The results of the experiments on surface tension, electrical conductivity and color are shown in Table 13.

TABLE 13

Surface tension, electrical conductivity and color of isoparaffinic fractions

| Fractionation method | Fraction description | Surface tension (mN/m) | Electrical conductivity (pS/m) | Saybolt color (—) |
|---|---|---|---|---|
| — | Isoparaffinic mixture | 27.3 | 2 | 28 |
| PILOT SCALE | 1: IBP-200 | 24.3 | <1 | +30 |
| | 2: 200-230 | 25.9 | <1 | +30 |
| | 3: 230-260 | 26.5 | <1 | +30 |
| | 4: 260-FBP | 27.8 | 6 | 22 |
| ASTM D86 | 95% distillate of 260- | 27.9 | <1 | +30 |

TABLE 13-continued

Surface tension, electrical conductivity and color of isoparaffinic fractions

| Fraction-ation method | Fraction description | Surface tension (mN/m) | Electrical conductivity (pS/m) | Saybolt color (—) |
|---|---|---|---|---|
| Apparatus | FBP | | | |
| | 5% Residue of 260-FBP | 28.3 | — | — |
| | 40% distillate of 260-FBP | 27.6 | — | — |
| | 60% residue of 260-FBP | 27.9 | — | — |
| TEST EQUIPMENT 1 | 1: 260-285 | 25.4 | <1 | +30 |
| | 2: 285-FBP | 24.9 | 11 | 17 |
| | 5% residue of 280-FBP by D86 | 23.3 | — | — |
| TEST EQUIPMENT 1 & TEST EQUIPMENT 2 | 190-220 | 24.5 | — | — |
| | 220-240 | 24.6 | — | — |

Isoparaffinic fractions obtained from Pilot Scale have the surface tensions ranging from 24.3 to 27.8 mN/m and the heavier fractions have higher surface tension. Similar trend can also be found in the fractions obtained from ASTM D86 apparatus. However, the surface tension of fractions obtained from Test Equipment 1 & Test Equipment 2 units shows lower surface tensions in the range of 23-25 mN/m which are not consistent with their boiling ranges. In addition, heavier fraction has lower surface tension than the lighter one. This leads to the assumption that there was a contamination during laboratory scale fractionation. The possible contaminant is the grease used for securing vacuum between the distillation column parts.

As for the electrical conductivity and color, small electrical conductivity and yellow color are already presented in the isoparaffinic mixture feedstock. It can be seen that the components which account for these properties tend to concentrate in the heaviest fraction. In addition, it was presented that the heaviest components left in the residue are responsible for both properties. These heaviest components are possibly polycyclic aromatic hydrocarbons which have high boiling temperatures and conductive properties ([Cited Document 107]).

Another possible reason for electrical conductivity is the antistatic additive. However, it is not present in this feedstock. The minimum electrical conductivity after addition of this additive can be around 100 pS/m according to ISO 6297 ([Cited Document 108]). Therefore, the electrical conductivity is not resulted from the additive. However, in the case that the feedstock contains an antistatic additive, the effect then depends on which active components contained in that additive. The active ingredient in the sulphonic type antistatic additive is for example Dinonylnaphthylsulfonic acid which tends to decompose before boiling at temperature higher than 300° C. ([Cited Document 109]). Therefore, the conductive property can be detected in the heaviest fraction.

The physical properties of n-paraffinic fractions are presented in Table 14. The trends of the relations between the physical properties and the boiling ranges are similar to isoparaffinic fractions. Due to high pour point of C18 and heavier components fraction, this fraction becomes solid at room temperature and some properties for example surface tension, KB and refractive index were not analyzed.

TABLE 14

Physical properties of n-paraffinic fractions

| No. | Physical Properties | unit | n-paraffinic mixture | C16 and lighter | C16-C18 | C18 and heavier |
|---|---|---|---|---|---|---|
| 1 | IBP | ° C. | 272.9 | 231.1 | 285.7 | 304.1 |
| | FBP | ° C. | 314.7 | 279.2 | 300.7 | 328.9 |
| 2 | Flash Point | ° C. | 113.0 | 101.0 | 139.0 | 157.0 |
| 3 | Aniline Point | ° C. | 98.5 | 93.1 | 98.0 | 100.9 |
| 4 | Kinematic Viscosity @ 20° C. | mm$^2$/s | N/A | 3.694 | 5.229 | N/A |
| | Kinematic Viscosity @ 40° C. | mm$^2$/s | 3.447 | 2.493 | 3.362 | 4.068 |
| | Kinematic Viscosity @ 100° C. | mm$^2$/s | — | 1.114 | 1.380 | 1.570 |
| 5 | Viscosity index | — | — | N/A | N/A | N/A |
| 6 | Density @ 15° C. | kg/m$^3$ | N/A | — | — | N/A |
| | Density @ 20° C. | kg/m$^3$ | N/A | 768.8 | 777.5 | N/A |
| | Density @ 50° C. | kg/m$^3$ | 757.8 | 748.0 | 756.9 | 762.6 |
| 7 | Surface Tension @ 23° C. | mN/m | 27.8 | 24.9 | 25.9 | N/A |
| 8 | Electrical conductivity @ 23° C. | pS/m | <1 | <1 | <1 | <1 |
| 9 | Kauri-Butanol Solubility test | — | — | 19.0 | 17.5 | N/A |
| 10 | Pour point | ° C. | — | 8.0 | 19.0 | 26.0 |
| 11 | Cloud point | ° C. | — | 8.3 | 20.1 | 29.5 |
| 12 | Relative evaporation rate of solvents to diethyether | — | — | >600 | >600 | N/A |
| 13 | Color | Saybolt | +30 | +30 | +30 | N/A |
| 16 | Vapor Pressure | kPa | 0.000 | 0.001 | 0.000 | 0.000 |
| 17 | Refractive index @ 20° C. | — | — | 1.4320 | 1.4365 | N/A |
| 20 | Solubility parameter | (MJ/m$^3$)$^{1/2}$ | — | 13.9 | 13.8 | — |

Flash point ranges from 101 to 157° C. and the aniline point varies from 93 to 101° C. as a function of increasing boiling range. Kinematic viscosity increases from 1.11 to 5.23 mm²/s depending on the boiling range. Likewise for isoparaffinic fractions, the viscosity index cannot be calculated. The density at 50° C. varies from 748 to 762 kg/m³. Significant higher pour points and cloud points than those of isoparaffinic fractions can be observed. Relative evaporation rates are also found to be higher than the upper limit. All the n-paraffinic fractions can be classified as non-VOCs as their vapor pressures are less than 0.01 kPa. In addition, the refractive index increases from 1.432 to 1.436 from the first to second fraction.

To obtain surface tension values, n-paraffinic mixture was also fractionated by laboratory scale fractionation unit. It can be assumed that the contamination can also occur and affect the surface tension analysis as well as for isoparaffinic fractions. The electrical conductivity was found to be less than 1 pS/m for both feedstock and n-paraffinic fractions.

Color with +30 in Saybolt color scale was observed in all the fractions including the feedstock. Furthermore, KB and solubility parameters are discovered to be slightly lower than for isoparaffinic fractions. KB and solubility parameter of first and second fractions are 19 and 17.5 for KB and 13.9 and 13.8 (MJ/m³)$^{1/2}$ for solubility parameter, respectively.

Example 3

Component Analysis

For isoparaffinic fractions, the carbon number distributions are corresponding with their boiling ranges. The results of the fraction with boiling range of IBP-200° C. using NM490B and NM291 are consistent. It has approximately 87 wt. % of isoparaffins, 12 wt. % of n-paraffins and 1 wt. % of naphthenes. Trace amount of olefins, aromatics and oxygenated compound are also found at 0.3, 0.03 and 0.07 wt. %, respectively. The component and structure analysis of isoparaffinic fractions are presented in Table 15.

TABLE 15

Component and Structure analysis of isoparaffinic fractions

| No. | Physical Properties | Unit | Iso-paraffinic mixture | Pilot scale (IBP-200) | | Pilot scale (200-230) | Pilot scale (230-260) | Pilot scale (260-FBP) | Test Equipment 1 (260-285) | Test Equipment 1 (285-FBP) |
|---|---|---|---|---|---|---|---|---|---|---|
| | | | | \multicolumn{7}{c|}{Carbon number distribution} | | | | | |
| 1 | Main carbon number (more than 10 wt. %) | — | — | C9-C12 | | C12-C14 | C13-C15 | C15-C18 | C15-C17 | C17-C18 |
| | Molecule structure | | | NM 490B | NM291 | | | NM490B | | |
| 1 | Isoparaffins- general | wt. % | — | 32.9 | — | 1.7 | 0.1 | 0.1 | 0.0 | 0.2 |
| 2 | Methyl paraffins | wt. % | — | 20.8 | — | 40.8 | 45.8 | 41.3 | 37.8 | 43.4 |
| 3 | Di/trimethyl paraffins | wt. % | — | 31.6 | — | 41.2 | 36.4 | 37.4 | 41.1 | 34.9 |
| 4 | Tri+ methyl paraffins | wt. % | — | 1.3 | — | 8.4 | 12.2 | 14.6 | 15.1 | 15.2 |
| | Total Isoparaffins | wt. % | — | 86.6 | 86.9 | 92.1 | 94.5 | 93.4 | 93.9 | 93.7 |
| 5 | n-paraffins | wt. % | — | 12.0 | 11.7 | 7.8 | 5.0 | 6.6 | 6.1 | 6.3 |
| 6 | Naphtenes | wt. % | — | 1.4 | 1.0 | 0.1 | 0.5 | — | — | — |
| 7 | Olefins | wt. % | — | — | 0.3 | — | — | — | — | — |
| 8 | Aromatics | wt. % | — | — | 0.03 | — | — | — | — | — |
| 9 | Oxygenated compound | wt. % | — | — | 0.07 | — | — | — | — | — |
| | | | | \multicolumn{7}{c|}{Specific component} | | | | | |
| 1 | Aromatic content | vol. % | 0.1 | 0.06 | | 0.11 | 0.11 | 0.11 | 0.18 | 0.02 |
| | | ppmv | 1000 | 600 | | 1100 | 1100 | 1100 | 1800 | 200 |
| | | ppm | 1131* | 713* | | 1273* | 1258* | 1236* | 2032* | 224* |
| 2 | Bromine Index | mg Br/100 g | 16 | 530 | | 180 | 107 | 21 | 35 | 17 |
| 3 | Sulphur content | mg/kg | <1 | <1 | | <1 | <1 | <1 | — | — |
| 4 | Benzene content | mg/L | <1 | <1 | | <1 | <1 | <1 | — | — |
| | | ppm | <1.29* | <1.35* | | <1.32* | <1.3* | <1.28* | — | — |

Note:

*Estimation as per Appendix F.2 aromatic content in ppm weight basis and Appendix F.3 benzene content in ppm weight basis (with density at 15° C.) of the Aalto University Thesis, the entire contents of which are incorporated herein by reference. Specifically, for aromatic content in ppm weight basis, the conversion from volume to weight basis is calculated as per equation below.

$$A(\text{wt. \%}) = \frac{A(\text{vol \%}) * 880}{D} \quad (F.1)$$

where A is the aromatic content, 880 is the density of monoaromatic (kg/m$^3$), D is the density of sample (kg/m$^3$). For benzene content in ppm weight basis, the conversion from volume to mass basis is calculated as per equation below.

$$B(\text{mg/kg}) = \frac{B(\text{mg/L})}{D} \quad (F.2)$$

Where B is the benzene content, and D is the density of sample (kg/L).

Other fractions have higher isoparaffins content being between 92-95 wt. % and lower n-paraffins content being roughly between 5-6 wt. %. Trace amount of naphthenes are found except for the fractions with boiling range higher than 260° C. In addition, sulphur contents are less than 1 ppm and the benzene contents are less than 1 mg/L.

The component and structure analysis of n-paraffinic fractions are presented in Table 16.

As for n-paraffinic fractions, the n-paraffins content is around 94-97 wt. % and isoparaffins content is between 3 and 6 wt. %. The sulphur and benzene contents were analyzed only for the n-paraffinic mixture and the results show less than 1 ppm and 1 mg/L, respectively. However, the sulphur and benzene contents of the n-paraffinic fractions can be implied to be as low as their feedstock.

Aromatic content balance was calculated and shown in Table 17. It can be seen that high aromatic content is originating from the high aromatic in the feedstock itself and no significant amount of aromatics was produced during the distillation.

TABLE 17

Aromatic content balance

| | Fractionation unit | Feedstock (ppmv) | avg. products (ppmv) |
|---|---|---|---|
| Isoparaffinic mixture | PILOT SCALE TEST EQUIPMENT 1 | 1000 1100 | 1061 842 |
| N-paraffinic mixture | TEST EQUIPMENT 2 | 2500 | 2821 |

On the other hand, bromine index balance is shown in Table 18. A significant amount of unsaturates or olefins

TABLE 16

Component and Structure analysis of n-paraffinic fractions

| No. | Physical Properties | Unit | n-paraffinic mixture | C16 and lighter | C16-C18 | C18 and heavier |
|---|---|---|---|---|---|---|
| | | | Carbon number distribution | | | |
| 1 | Main carbon number (more than 10 wt. %) | — | — | C14-C16 | C16-C18 | C18 |
| Molecule structure | | | | NM490B | | |
| 1 | Isoparaffins-general | wt. % | — | 0.6 | 0.0 | 0.9 |
| 2 | Methyl paraffins | wt. % | — | 4.2 | 2.6 | 1.5 |
| 3 | Di/tri methyl paraffins | wt. % | — | 1.1 | 0.5 | 0.4 |
| 4 | Tri+ methyl paraffins | wt. % | — | 0.3 | 0.2 | 0.2 |
| | Total Isoparaffins | wt. % | — | 6.2 | 3.3 | 3.0 |
| 5 | n-paraffins | wt. % | — | 93.8 | 96.7 | 97.0 |
| | | | Specific component | | | |
| 1 | Aromatic content | vol. % | 0.25 | 0.1 | 0.03 | 0.56 |
| | | ppmv | 2500 | 1000 | 300 | 5600 |
| | | ppm | 2903* | 1176* | 349* | 6462* |
| 2 | Bromine Index | mg Br/100 g | 5 | 8 | 5 | — |
| 3 | Sulphur content | mg/kg | <1 | — | — | — |
| 4 | Benzene content | mg/L | <1 | — | — | — |
| | | ppm | <1.32* | — | — | — |

Note:
*Estimation as per Appendix F.2 and Appendix F.3 (with density at 50° C.) of the Aalto University Thesis, discussed above, the entire contents of which are incorporated herein by reference.

produced during fractionation in Pilot Scale unit and ASTM D86 apparatus was discovered. While, no considerable amount of olefins was formed in Test Equipment 1 and Test Equipment 2 units.

TABLE 18

Bromine Index balance

| | Fractionation unit | Feedstock (mg Br/ 100 g) | Products (mg Br/ 100 g) |
|---|---|---|---|
| Isoparaffinic mixture | PILOT SCALE | 16 | 71 (avg.) |
| | TEST EQUIPMENT 1 | 21 | 24 (avg.) |
| | TEST EQUIPMENT 1 & TEST EQUIPMENT 2 | 16 | 20 (190-220° C.) 17 (220-240° C.) |
| Isoparaffins (260-FBP) | ASTM D86 | 21 | 67 |
| Isoparaffins (285-FBP) | ASTM D86 | 17 | 93 |
| N-paraffinic mixture | TEST EQUIPMENT 2 | 5 | 5 (C16 and lighter) 8 (C16-C18) |

Figure 4:
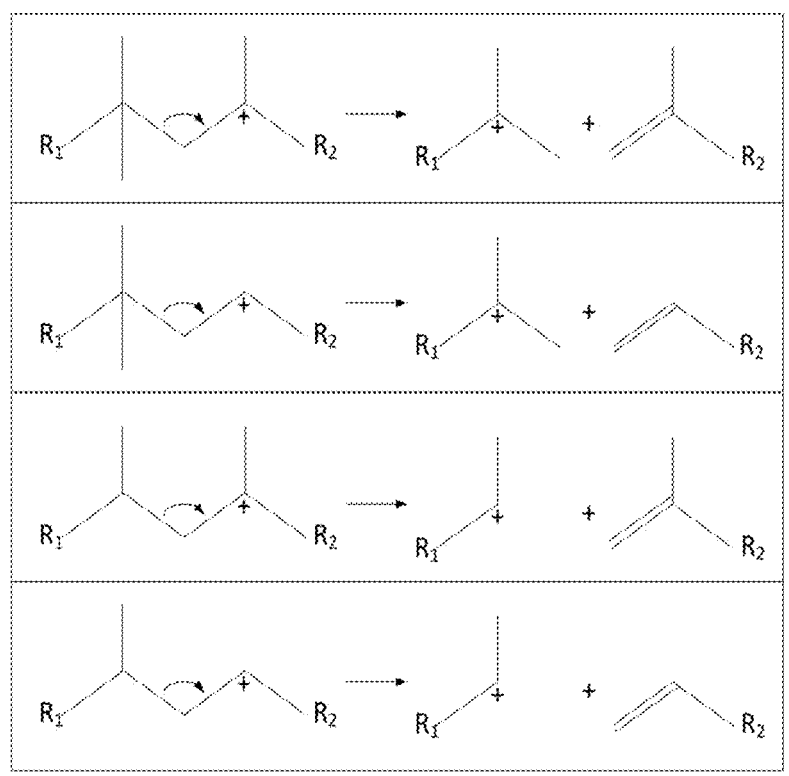
FIG. 4 depicts potential cracking reactions of isoparaffins, according to an exemplary aspect.

The olefins produced are possible originating from cracking due to heating in the fractionation. Potential cracking reactions are shown in FIG. 4 (Cracking of isoparaffins ([Cited Document 110])). Cracking produces shorter carbon chain isoparaffins, olefins and n-paraffins. The olefins and n-paraffins then tend to be present in the lighter fraction more than heavier fraction due to the shorter carbon number. This is consistent with results shown in the component analysis that the lightest fraction has the highest olefins and n-paraffins content.

The heating temperature during laboratory scale fractionations is between 180-195° C. for isoparaffinic mixture and between 195-220° C. for n-paraffinic mixture and the duration of fractionation is around 24 hours, whereas, the heating temperatures during ASTM D86 distillation are between 280-300° C. and the distillation duration is only 1 hour. Also, the heating temperature is potentially much higher near the surface of the electrical heater. This means that the mixtures are sensitive to heat and cracking easily occurs when subjecting to the heat in the range of 200-300° C. However, significant shorter residence time is expected in industrial scale distillation and it can be done by vacuum distillation to reduce the bottom temperature if necessary.

The olefins content can also be responsible for the odor presents in the fractions. The fractions with boiling range of IBP-200° C. and 200-230° C. having bromine index at 530 and 180 mg Br/100 g, respectively, have the odor, while the heavier fractions which have lower bromine index are odorless.

Example 4

Comparison to Commercial Products

Physical properties and component of the fractions are compared with isoparaffinic commercial products from companies discussed in Section 5.2 ("Manufacturers and Commercial aliphatic fluids") of the Aalto University Thesis, the entire contents of which are incorporated herein by reference. The details of the comparison are presented in Appendix H of the Aalto University Thesis. The information is gathered from the manufactures' websites, therefore, not all of physical properties and component are reported. In general, the physical properties for example flash point, aniline point, viscosity, density are comparable with the commercial products. However, there are some differences in the properties and components discussed in the following paragraphs.

Comparing to ShellSol from Shell Chemicals, ShellSol products show slightly lower surface tension and higher KB and solubility parameter. In term of composition, ShellSol T and TD have bromine indexes of 300 and 400 ppm, respectively. They are lower than the fraction with boiling range from IBP to 200° C. However, they are higher than other fractions. ShellSol products offer lower aromatic content except for ShellSol OMS and TK which have the aromatic content up to 1000 ppm and 2500 ppmv.

Isopar products from ExxonMobil Chemical have significantly lower aromatic content from 10 to 40 ppm for most of the grades except for Isopar V which has aromatic content up to 1000 ppm. In addition, ISANE from TOTAL Special Fluids are claimed to have 100% of isoparaffins as their typical property. The bromine index and aromatic content are significant lower with the specifications of 20 mg Br/100 g and from 10 to 100 ppm for aromatic content depending on the grades.

Soltrol 100 and Soltrol 125 from Chevron Phillips Chemical offer higher purity with more than 99 wt. % of isoparaffins and the aromatic content varying from 25 to 250 ppm. However, the Soltrol 220 which is the heaviest grade has 2000 ppm of aromatic content and up to 15 ppm of sulphur. INEOS isoparaffins products provide very low aromatic content around 1 ppm for most of their products. However, the bromine indexes are higher with bromine number varying from 0.5 to 2 g Br/100 g (roughly 500 to 2000 mg Br/100 g) depending on the product. Also, specifications of sulphur content are higher being between 3 and 5 ppm. Only isododecane has low bromine index of 15 mg Br/100 g and 1 ppm of sulphur content.

For printing ink distillates from Haltermann, all grades except the PRWF 1/3 af have around 75 wt. % of paraffins and 25 wt. % of naphthenes. While, PRWF 1/3 af which is the lightest grade have 99 wt. % of paraffins and less than 1 wt. % of naphthenes. In addition, they have higher both bromine index and aromatic content. The range of bromine index is from 0.5 to 1 g Br/100 g (roughly 500 to 1000 mg Br/100 g), while the range of aromatic content is from 1000 (0.1 wt. %) to 10000 ppm (1 wt. %) for other grades except PRWF 5/9 which has high aromatic content up to 10 wt. %. Pour points of Haltermann's products are also higher varying from −6° C. to less than −25° C. The color of the products also varies from clear water white for lightest grade, virtually water white for middle range grades and pale yellow for the heaviest grade.

Example 5

Applicability Evaluation

The preliminary applicability evaluation is based on chemical compatibility with different materials, ability of forming emulsions and lastly, the pigment dispersion stability.

Figure 9:
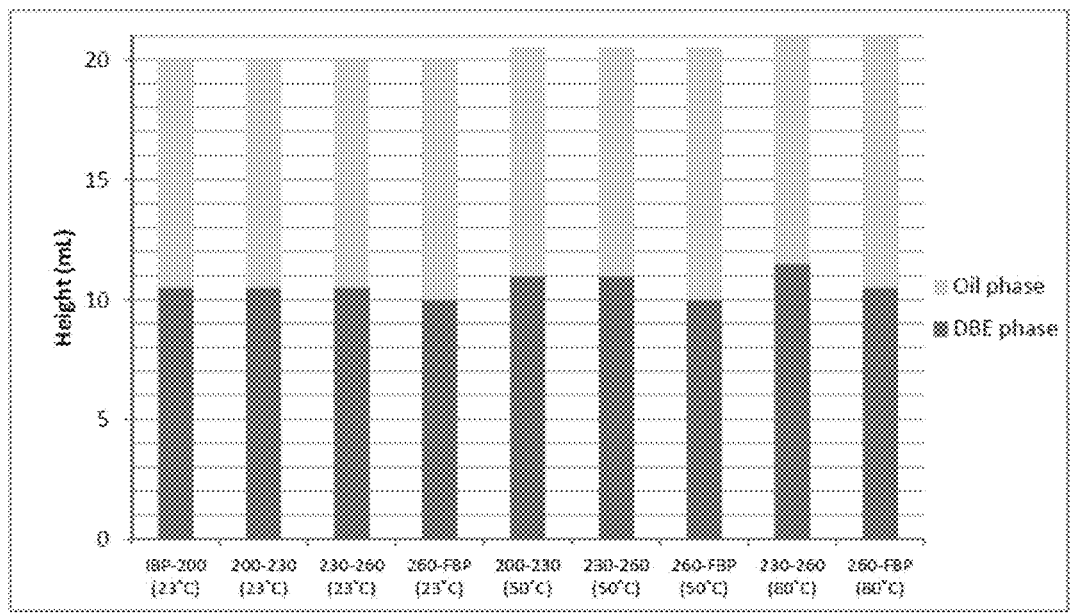
FIG. 9 depicts a graph in connection with liquid solubility with DBE® Esters at different temperatures and fractions, according to an exemplary aspect.
Figure 10:
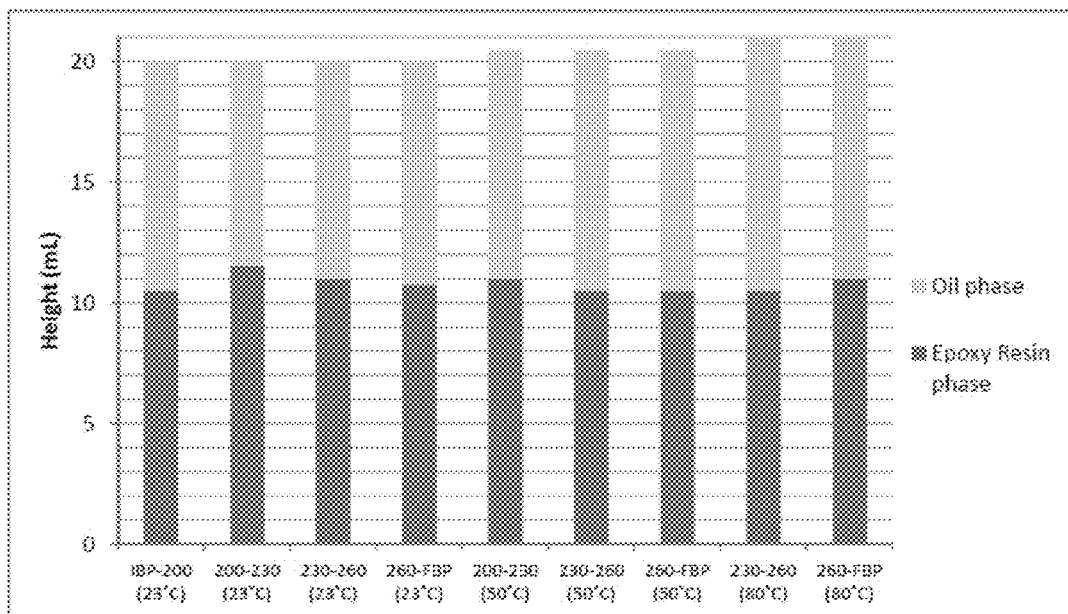
FIG. 10 depicts a graph in connection with liquid solubility with Epoxy resin at different temperatures and fractions, according to an exemplary aspect.

Table 19 shows the solubility results from chemical compatibility test with liquid materials. It was found that all the fractions are readily soluble in silicone fluid, tall oil fatty acid and Rapeseed oil at room temperature (around 23° C.). However, the fractions are sparingly soluble or insoluble in DBE and Epoxy resin. Generally for all the fractions, around 5 vol. % of isoparaffinic fraction is able to dissolve in DBE phase at room temperature. However, increasing in temperature of the solution does not significantly increase the solubility. For solubility with epoxy resin, small amount of isoparaffinic fraction can dissolve in Epoxy resin at room temperature at around 5-10 vol. % dependent on fractions. In addition, due to increasing in temperature, small amount of epoxy resin is able to dissolve in fractions, however, no significant changing in solubility occurred at elevated temperature. The detailed results for DBE and epoxy resin solubility are shown in FIG. 9 (Liquid solubility with DBE® Esters at different temperatures and fractions) and FIG. 10 (Liquid solubility with Epoxy resin at different temperatures and fractions).

For thermoplastic polyurethanes, no effect was discovered at room temperature and minor effect at higher temperature is observed. Moreover, it is found that Kraton® polymers are able to form viscous liquid and gel with the fractions. In other words, Kraton® polymers are able to be used as thickening or gelling agent together with the isoparaffinic fractions. The lightest fraction with boiling range of IBP-200° C. is compatible with these polymers at room temperature, while heavier fractions can require higher temperature to form gel or viscous liquid. All the liquids or viscous liquids become hard gels when cooling down to room temperature.

TABLE 19

Solubility between fractions and various liquids.

| | Fraction | | | | | | | | |
|---|---|---|---|---|---|---|---|---|---|
| | PILOT SCALE (IBP-200) | PILOT SCALE (200-230) | | PILOT SCALE (230-260) | | | PILOT SCALE (260-FBP) | | |
| | | | | Temp. (° C.) | | | | | |
| Test Liquid | 23 | 23 | 50 | 23 | 50 | 80 | 23 | 50 | 80 |
| Silicone Fluid | Soluble | Soluble | — | Soluble | — | — | Soluble | — | — |
| Tall Oil fatty acid | Soluble | Soluble | — | Soluble | — | — | Soluble | — | — |
| Rapeseed Oil | Soluble | Soluble | — | Soluble | — | — | Soluble | — | — |
| DBE Esters | Sparingly soluble | Sparingly soluble | Sparingly soluble | Sparingly soluble | Sparingly soluble | Sparingly soluble | Insoluble | Insoluble | Sparingly soluble |
| Epoxy Resin | Sparingly soluble | Sparingly soluble | Sparingly soluble | Sparingly soluble | Sparingly soluble | Sparingly soluble | Sparingly soluble | Sparingly soluble | Sparingly soluble |

Table 20 shows the compatibility results between different fractions and various plastics and elastomers. The results are divided in to 3 parts based on the material types which are elastomers, thermoplastic elastomers and plastics. For elastomers, all the fractions are compatible in term of highly swelling with non-polar elastomers which are EPDM, SIL and NR. Less swelling occurred with CR and between no to minor effect occurred with NBR. Both of them are polar elastomers.

For other plastics, the fractions do not affect most of plastics including PUR, PA610, PC, PET, PMMA and PVAc. Higher temperature does not increase the solubility between the fractions and these plastics. However, the fractions have some swelling effect to PS, PE and PP. Partial dissolution was found with PVC and it is likely that the fractions dissolve the plasticizer in PVC rather than the PVC itself. Lastly, no slightly swelling was found with RADILON polyamide products.

TABLE 20

Solubility between fractions and plastics and elastomers

| | % Weight change | | | | | | | | | | |
|---|---|---|---|---|---|---|---|---|---|---|---|
| | Fraction | | | | | | | | | | |
| | PILOT SCALE (IBP-200) | PILOT SCALE (200-230) | | PILOT SCALE (230-260) | | | PILOT SCALE (260-FBP) | | | ShellSol T | ShellSol A 100 |
| | | | | Temperature | | | | | | | |
| Materials | 23 | 23 | 50 | 23 | 50 | 80 | 23 | 50 | 80 | 23 | 23 |
| Elastomers | | | | | | | | | | | |
| NBR | −4.4 | 0.0 | −0.7 | 0.0 | −0.7 | −3.3 | 0.0 | 0.0 | −3.3 | −0.7 | 45.9 |
| CR | 16.7 | 10.5 | 15.3 | 10.7 | 16.7 | 15.3 | 8.0 | 11.3 | 12.4 | 10.3 | 82.1 |
| EPDM | 50.0 | 49.3 | 51.0 | 48.3 | 51.3 | 51.0 | 48.7 | 50.7 | 49.7 | 46.4 | 75.2 |
| SIL | 93.3 | 76.7 | 79.4 | 67.1 | 71.8 | 75.9 | 40.7 | 48.2 | 52.4 | 92.1 | 94.1 |
| NR PARA | 120.0 | 103.3 | 116.9 | 89.3 | 109.9 | 119.6 | 66.9 | 90.5 | 106.6 | 109.0 | 265.3 |
| NR NAT 1729 | 40.0 | 39.3 | 47.4 | 35.3 | 46.4 | 56.7 | 26.0 | 41.1 | 53.3 | 38.9 | 112.2 |
| Thermoplastic Elastomer | | | | | | | | | | | |
| TPU-blue tube | 0.7 | 0.0 | 2.7 | 0.7 | 2.0 | 2.7 | 0.7 | 2.0 | 2.7 | 0.0 | 26.5 |
| TPU-colorless tube | 0.0 | 0.0 | 0.5 | 0.0 | 0.7 | 0.7 | 0.7 | 0.7 | 0.7 | — | — |

TABLE 20-continued

Solubility between fractions and plastics and elastomers

| | % Weight change Fraction | | | | | | | | | | |
|---|---|---|---|---|---|---|---|---|---|---|---|
| | PILOT SCALE (IBP-200) | PILOT SCALE (200-230) | | PILOT SCALE (230-260) | | | PILOT SCALE (260-FBP) | | | ShellSol T | ShellSol A 100 |
| | | | | | Temperature | | | | | | |
| Materials | 23 | 23 | 50 | 23 | 50 | 80 | 23 | 50 | 80 | 23 | 23 |
| KRATON Polymers | | | | | | | | | | | |
| SBS D1102 | G | S | VL | S | G | VL | S | S | VL | S | DS |
| SEBS G1654 | G | S | G | S | G | VL | S | S + G | G | S | DS |
| SEBS G1650 | VL | G | VL | G | VL | L | S | VL (opaque) | L | G | DS |
| SEBS FG1901 | G + VL | G | VL | S | VL | L | S | G + VL | VL | S | DS |
| Plastics | | | | | | | | | | | |
| PUR | 0.0 | 0.0 | 0.0 | 0.0 | 0.0 | 0.0 | 0.0 | 0.0 | 0.0 | 0.0 | 3.0 |
| PA610 tube | 0.0 | 0.0 | 0.0 | 0.0 | 0.0 | −0.5 | 0.0 | 0.0 | −0.5 | 0.0 | 0.0 |
| PC | 0.0 | 0.7 | 0.7 | 0.0 | 0.0 | 0.0 | 0.0 | 0.0 | −0.6 | 0.0 | 20.4 |
| PET | 0.7 | 0.7 | 0.7 | 0.0 | 0.7 | 0.7 | 0.7 | 0.7 | 0.7 | 0.6 | 6.6 |
| PMMA | 0.7 | 0.0 | 0.0 | 0.0 | 0.0 | −0.7 | 0.0 | 0.0 | 0.0 | 0.0 | 0.7 |
| PS | 0.7 | 0.7 | 2.0 | 0.0 | 1.3 | 7.9 | 0.7 | 0.0 | 2.0 | 0.7 | DS |
| PE | 0.8 | 0.8 | 1.2 | 0.8 | 2.0 | 3.1 | 0.0 | 1.3 | 3.8 | 0.8 | 4.1 |
| PP | 3.9 | 2.9 | 11.8 | 1.0 | 6.1 | 12.2 | 1.0 | 5.1 | 11.1 | 3.8 | 5.0 |
| PVC | −10.0 | −4.0 | −16.0 | −3.3 | −14.0 | −14.7 | −3.3 | −10.0 | −10.0 | −6.7 | 3.2 |
| PVAc | N/A | N/A | N/A | N/A | N/A | N/A | N/A | N/A | N/A | N/A | 38.2 |
| RADILON Polyamide** | | | | | | | | | | | |
| PA6 | 0.7 | 0.6 | | 1.0 | | | 1.0 | | | 1.4 | 3.3 |
| PA66 | 0.8 | 1.5 | | 0.8 | | | 1.7 | | | 0.7 | 2.0 |
| PA610 | 0.5 | 0.6 | | 1.4 | | | 1.5 | | | 0.7 | 2.0 |

Note:
N/A: measuring the weight is not practical but the visual result is observed, G: the solution becomes gel, VL: the solution becomes viscous liquid, L: the solution become liquid, S: the swelling is occurred but the weight cannot be measured, DS: the polymer is dissolved in the fraction and —: no experiment is conducted.

Comparing to ShellSol T which is isoparaffinic solvent with boiling range from 189 to 215° C., the compatibility level of ShellSol T is between the first (IBP-200° C.) and second (200-230° C.) fraction when their boiling ranges are used as a criteria. It was found that the compatibilities of the ShellSol T, first and second fractions are comparable for most of materials. However, ShellSol T shows less compatibility with Kraton® polymer than the second fraction since it can form gel with SEBS G1650 only and causes swelling for other Kraton® polymers.

As a result of high dissolving power of aromatic components, ShellSol A 100 shows more compatibility to all of the materials than isoparaffinic fractions. It is able to dissolve polystyrene and all of Kraton® polymers without forming any viscous liquid or gel. It has no effect only with PA 610 and PMMA at room temperature.

Table 21 shows the time when emulsions between fraction and emulsifier start to break. It shows that emulsifiers which form emulsions from the highest to lowest stability are MULSIFAN CB, Berol 791 and SIMULSOL 165, respectively. For Berol 791, W/O emulsions perform better than O/W emulsion. This is due to the fact that this liquid emulsifier is readily dissolved in oil phase and not in water phase. Stability of emulsions with MULSIFAN CB depends on the fractions. W/O emulsions show better stability with the 2 heaviest fractions, while O/W emulsion performs better for fraction with boiling range of 200-230° C. However, the lightest fraction was not tested for O/W emulsion. Lastly, for SIMULSOL 165, O/W emulsions perform better than W/O emulsions.

TABLE 21

Emulsion break of the combination

| | Type of Emulsion | | | | | | | |
|---|---|---|---|---|---|---|---|---|
| | W/O | | | | O/W | | | |
| | Fraction | | | | | | | |
| Emulsifier | PILOT SCALE (IBP-200) | PILOT SCALE (200-230) | PILOT SCALE (230-260) | PILOT SCALE (260-FBP) | PILOT SCALE (IBP-200) | PILOT SCALE (200-230) | PILOT SCALE (230-260) | PILOT SCALE (260-FBP) |
| No emulsifier | less than 5 min. at 22° C. | | | | | | | |
| Berol 791 | 24 h at 23° C. | 24 h at 4° C. | 24 h at 4° C. | 24 h at 4° C. | 1 h. at 23° C. | 1 h. at 23° C. | 1 h. at 23° C. | 30 min at 23° C. |
| MULSIFAN CB | N/A | 20 min. at 23° C. | $2^{nd}$ freeze/thaw cycle | $3^{rd}$ freeze/thaw cycle | $1^{st}$ freeze/thaw cycle | $1^{st}$ freeze/thaw cycle | $1^{st}$ freeze/thaw cycle | $1^{st}$ freeze/thaw cycle |
| SIMULSOL 165 | N/A | N/A | 5 min. at 23° C. | 5 min. at 23° C. | less than 5 min. at 23° C. | 1 h. at 23° C. | 24 h at 23° C. | 24 h at 23° C. |

Figure 5:
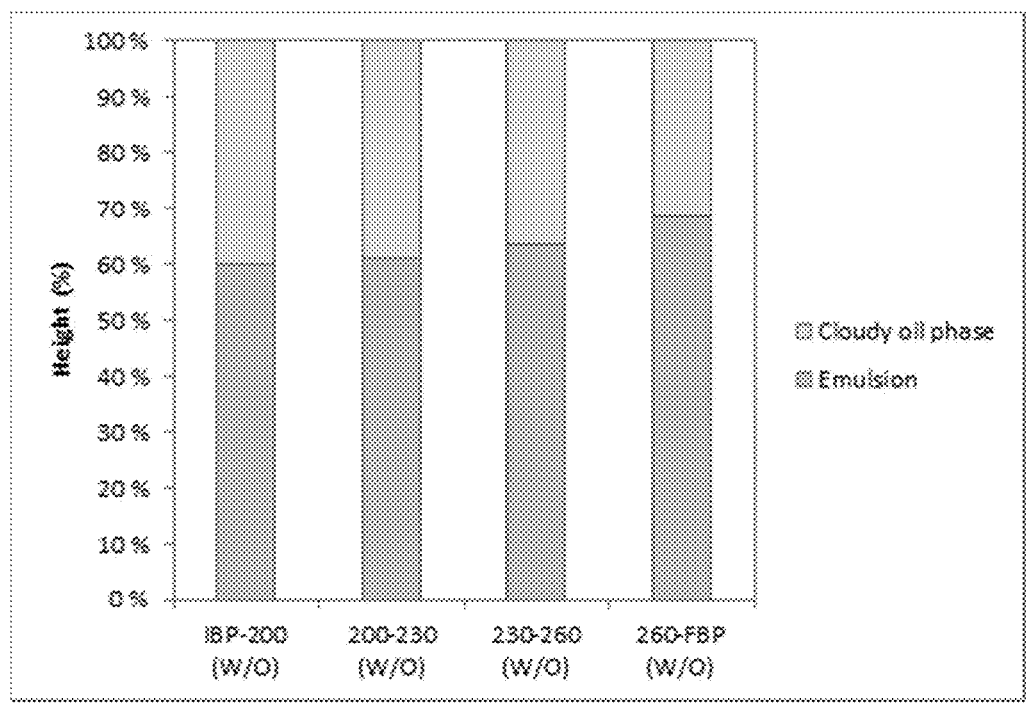
FIG. 5 depicts a graph in connection with different layers in W/O emulsions with Berol 791 after 24 hours at 4° C., according to an exemplary aspect.

FIG. 5 shows the height of different layers in W/O emulsions with Berol 791 after 24 hours at 4° C. and it can be seen from the graph that the heavier fraction shows more stability than the lighter one.

FIG. 6 shows the height of different layers of O/W emulsions with Berol 791 after 24 hour at room temperature (23° C.). Opposite from W/O emulsion, the lighter fraction shows more stability than heavier one.

Figure 7:
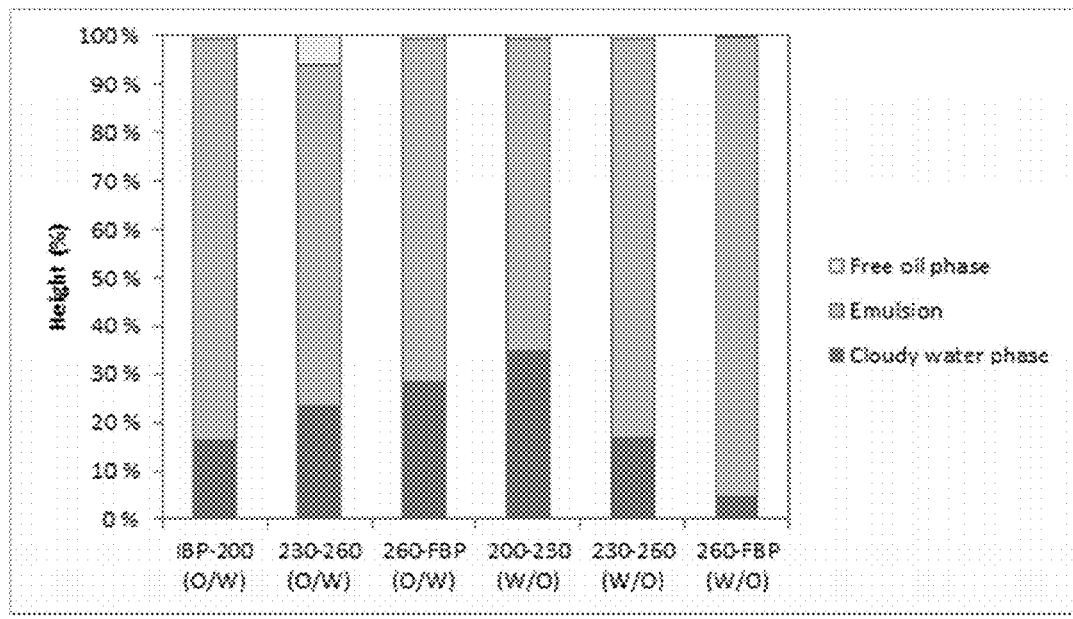
FIG. 7 depicts a graph in connection with different layers in O/W and W/O emulsions with MULSIFAN CB after $3^{rd}$ Freeze/Thaw cycle, according to an exemplary aspect.

Similar results in FIG. 7 (different layers in O/W and W/O emulsions with MULSIFAN CB after $3^{rd}$ Freeze/Thaw cycle) for MULSIFAN CB emulsifier show that heavier fraction has more stability than lighter ones in W/O emulsion, whereas, lighter fraction has more stability than heavier one for O/W emulsion.

Figure 8:
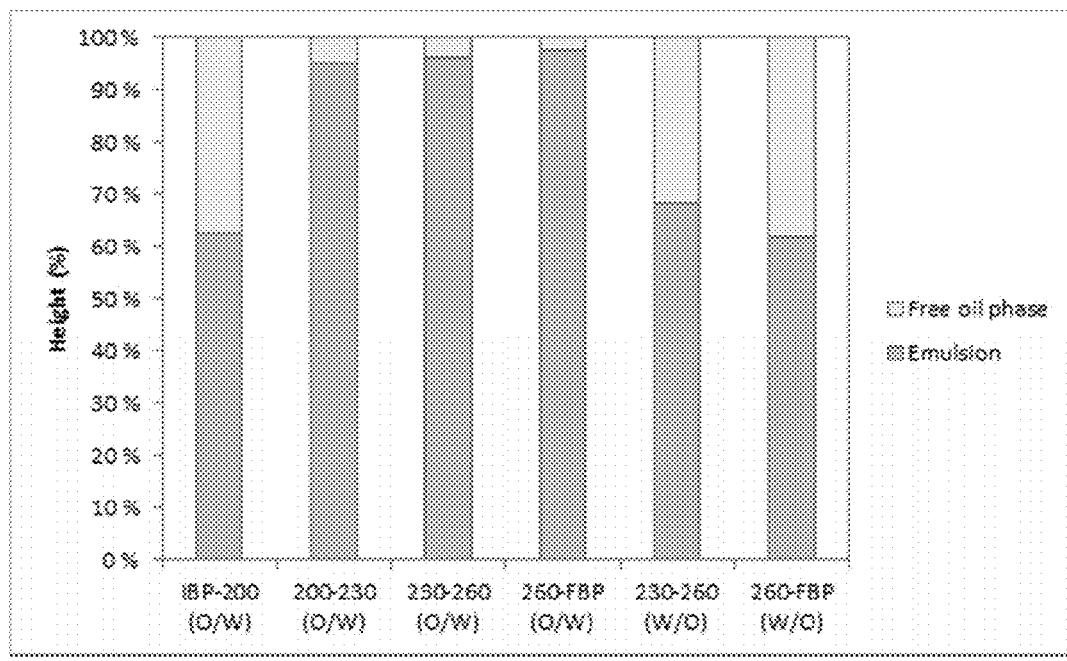
FIG. 8 depicts a graph in connection with different layers in O/W and W/O emulsions with SIMULSOL 165 after 24 hours at room temperature, according to an exemplary aspect.

FIG. 8 (different layers in O/W and W/O emulsions with SIMULSOL 165 after 24 hours at room temperature) shows the results with SIMULSOL 165 emulsifier. It can be seen that W/O emulsion exhibits better stability with lighter fraction than heavier one, while better stability is observed with heavier fraction than lighter one in O/W emulsion.

Table 22 presents the dispersion stability results for different fractions and pigments. The photographs recording the sedimentation behavior at specific time are depicted in Appendix J ("Photographs of pigment dispersion stability") of the Aalto University Thesis, the entire contents of which are incorporated herein by reference.

TABLE 22

Stability scale between different fraction and pigment

| | Pigment | |
|---|---|---|
| Fraction | Carbon black | Titanium dioxide |
| IBP-200 | Moderate stable | Moderate stable |
| 200-230 | Moderate stable | Moderate stable |
| 230-260 | Stable | Moderate stable |
| 260-FBP | Stable | Moderate stable |
| water | Unstable | Stable |
| paraffinic solvent | Moderate stable | Moderate stable |
| acetone | Unstable | Stable |
| xylene | Moderate stable | Moderate stable |

With both pigments, the heavier isoparaffinic fraction exhibits more dispersion stability than the lighter one. Carbon black pigment shows preferable interaction with non-polar solvent. As it can be seen, an unstable dispersion with water and acetone which are polar solvents are discovered, whereas, the pigment dispersion is more stable with non-polar solvents, i.e. with paraffinic solvent, xylene and isoparaffinic fractions especially the two heaviest fractions. On the contrary, results with titanium dioxide pigment show preferable interaction with polar solvents. However, the results exhibit moderate stable dispersion for non-polar solvents. As mentioned in the literature review, the surface tension is an important property during the pigment wetting and dispersion steps. The lower surface tension results in better pigment wetting and less energy that can be required for dispersion. However, the results from this preliminary test indicate that the polarity property has more effect on the dispersion stability than the surface tension.

In chemical compatibility tests, it was observed that the fractions are readily soluble in tall oil fatty acid, silicone fluid and rapeseed oil, while sparingly soluble in epoxy resin and DBE. For plastics and elastomers, the fractions show the compatibility in term of swelling with non-polar elastomers which are EPDM, Silicone rubber and Natural rubber. Moreover, they are compatible with Kraton® products to form viscous liquid and gel which indicates that the Kraton® products can be used as thickening and gelling agent together with these fractions. However, the fractions show no to minor effect to most of the plastics for example PUR, PA, PC, PET and PMMA. Swelling at higher temperature occurs with PS, PP and PE, while, they are able to partial dissolve the plasticizer in PVC.

In emulsion formation stability testing, it was found that emulsion is formed with different emulsifiers. However, the stability of emulsion is dependent on many parameters which are the type of emulsifier, order of addition or type of emulsion and the fractions itself. Generally, MULSIFAN CB exhibits the best stability followed by Berol 791 and SIMULSOL 165.

Pigment dispersion shows the level of moderate stable with titanium dioxide and moderate stable to stable with Carbon black. It was discovered that carbon black pigment exhibits better interaction with non-polar being isoparaffinic fractions, xylene and paraffinic solvents, while titanium dioxide has preferable interaction with polar solvents being acetone and water.

A separation process by distillation is conducted in order to obtain a composition rich in C14 and C15 isoparaffins. The Test Equipment 1 and Test Equipment 2 distillation apparatuses described above are employed. The process to obtain the C14-C15 fraction was similar to the one described above used for obtaining the other distilled fractions, e.g. the 230-260° C. fraction. Details concerning the resulting composition are set forth in the following Tables 23 and 24.

TABLE 23

Composition containing C14 and C15 isoparaffins

| Carbon number | iP | iP-di/trime | iP-me | iP-trime+ | Total iP | nP | Grand Total |
|---|---|---|---|---|---|---|---|
| 2 | 0.00 | 0.00 | 0.00 | 0.00 | 0.00 | 0.00 | 0.00 |
| 3 | 0.00 | 0.00 | 0.00 | 0.00 | 0.00 | 0.00 | 0.00 |
| 4 | 0.00 | 0.00 | 0.00 | 0.00 | 0.00 | 0.00 | 0.00 |
| 5 | 0.00 | 0.00 | 0.00 | 0.00 | 0.00 | 0.00 | 0.00 |
| 6 | 0.00 | 0.00 | 0.00 | 0.00 | 0.00 | 0.00 | 0.00 |
| 7 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 |
| 10 | 0.00 | 0.00 | 0.00 | 0.00 | 0.00 | 0.00 | 0.00 |
| 11 | 0.00 | 0.00 | 0.00 | 0.00 | 0.00 | 0.00 | 0.00 |
| 12 | 0.00 | 0.04 | 0.17 | 0.02 | 0.23 | 0.14 | 0.37 |
| 13 | 0.00 | 1.91 | 4.42 | 0.09 | 6.41 | 1.55 | 7.97 |
| 14 | 0.00 | 16.97 | 21.36 | 2.10 | 40.43 | 3.88 | 44.31 |
| 15 | 0.00 | 21.60 | 10.88 | 7.45 | 39.93 | 0.73 | 40.66 |
| 16 | 0.00 | 2.78 | 0.80 | 2.79 | 6.38 | 0.03 | 6.41 |
| 17 | 0.00 | 0.11 | 0.04 | 0.10 | 0.24 | 0.00 | 0.24 |
| 18 | 0.00 | 0.02 | 0.00 | 0.02 | 0.04 | 0.00 | 0.04 |
| 19 | 0.00 | 0.00 | 0.00 | 0.00 | 0.00 | 0.00 | 0.00 |
| 20 | 0.00 | 0.00 | 0.00 | 0.00 | 0.00 | 0.00 | 0.00 |
| 21 | 0.00 | 0.00 | 0.00 | 0.00 | 0.00 | 0.00 | 0.00 |
| 22 | 0.00 | 0.00 | 0.00 | 0.00 | 0.00 | 0.00 | 0.00 |
| 23 | 0.00 | 0.00 | 0.00 | 0.00 | 0.00 | 0.00 | 0.00 |
| 24 | 0.00 | 0.00 | 0.00 | 0.00 | 0.00 | 0.00 | 0.00 |
| 25 | 0.00 | 0.00 | 0.00 | 0.00 | 0.00 | 0.00 | 0.00 |
| >C36 | 0.00 | 0.00 | 0.00 | 0.00 | 0.00 | 0.00 | 0.00 |
| C25-C29 | 0.00 | 0.00 | 0.00 | 0.00 | 0.00 | 0.00 | 0.00 |
| C30-C36 | 0.00 | 0.00 | 0.00 | 0.00 | 0.00 | 0.00 | 0.00 |
|  | 0.00 | 43.42 | 37.68 | 12.56 | 93.67 | 6.33 | 100.00 |

In Table 23, "iP" refers to isoparaffins, and "me" refers to methylene groups, e.g., "iP-me" refers to an isoparaffin with one methylene group (branch).

TABLE 24

Composition containing C14 and C15 isoparaffins

| Component | Content (wt-%) |
|---|---|
| Total iP of C14 and C15 | 80.36 |
| Grand total of C14 and C15 | 84.97 |
| Grand total of C13 and smaller | 8.34 |
| Grand total of C16 and bigger | 6.69 |

A separation process by distillation is conducted in order to obtain a 190-220° C. fraction. The Test Equipment 1 and Test Equipment 2 distillation apparatuses described above are employed. The process to obtain the 190-220° C. fraction was similar to the one described above used for obtaining the other distilled fractions, e.g. the 230-260° C. fraction. Details concerning the resulting composition are set forth in the following Table 25.

TABLE 25

Composition of 190-220° C. fraction

| Carbon number | iP | iP-di/trime | iP-me | iP-trime+ | nP | Grand Total |
|---|---|---|---|---|---|---|
| 2 | 0.00 | 0.00 | 0.00 | 0.00 | 0.00 | 0.00 |
| 3 | 0.00 | 0.00 | 0.00 | 0.00 | 0.00 | 0.00 |
| 4 | 0.00 | 0.00 | 0.00 | 0.00 | 0.00 | 0.00 |
| 5 | 0.00 | 0.00 | 0.00 | 0.00 | 0.00 | 0.00 |
| 6 | 0.00 | 0.00 | 0.00 | 0.00 | 0.00 | 0.00 |
| 7 | 0.00 | 0.00 | 0.00 | 0.00 | 0.00 | 0.00 |
| 8 | 0.00 | 0.00 | 0.00 | 0.00 | 0.00 | 0.00 |
| 9 | 0.01 | 0.00 | 0.00 | 0.00 | 0.00 | 0.01 |
| 10 | 0.25 | 0.00 | 0.00 | 0.00 | 0.21 | 0.47 |
| 11 | 0.00 | 3.32 | 10.20 | 0.00 | 4.17 | 17.69 |
| 12 | 0.00 | 26.92 | 26.26 | 1.78 | 3.26 | 58.22 |
| 13 | 0.00 | 12.76 | 4.59 | 4.07 | 0.21 | 21.64 |
| 14 | 0.00 | 0.96 | 0.22 | 0.68 | 0.01 | 1.87 |
| 15 | 0.00 | 0.05 | 0.01 | 0.04 | 0.00 | 0.11 |
| 16 | 0.00 | 0.00 | 0.00 | 0.00 | 0.00 | 0.00 |
| 17 | 0.00 | 0.00 | 0.00 | 0.00 | 0.00 | 0.00 |
| 18 | 0.00 | 0.00 | 0.00 | 0.00 | 0.00 | 0.00 |
| 19 | 0.00 | 0.00 | 0.00 | 0.00 | 0.00 | 0.00 |
| 20 | 0.00 | 0.00 | 0.00 | 0.00 | 0.00 | 0.00 |
| 21 | 0.00 | 0.00 | 0.00 | 0.00 | 0.00 | 0.00 |
| 22 | 0.00 | 0.00 | 0.00 | 0.00 | 0.00 | 0.00 |
| 23 | 0.00 | 0.00 | 0.00 | 0.00 | 0.00 | 0.00 |
| 24 | 0.00 | 0.00 | 0.00 | 0.00 | 0.00 | 0.00 |
| 25 | 0.00 | 0.00 | 0.00 | 0.00 | 0.00 | 0.00 |
| >C36 | 0.00 | 0.00 | 0.00 | 0.00 | 0.00 | 0.00 |
| C25-C29 | 0.00 | 0.00 | 0.00 | 0.00 | 0.00 | 0.00 |
| C30-C36 | 0.00 | 0.00 | 0.00 | 0.00 | 0.00 | 0.00 |
| Grand Total | 0.26 | 44.01 | 41.28 | 6.58 | 7.87 | 100.00 |

In Table 25, "iP" refers to isoparaffins, and "me" refers to methylene groups, e.g., "iP-me" refers to an isoparaffin with one methylene group (branch).

A separation process by distillation is conducted in order to obtain a 220-240° C. fraction. The Test Equipment 1 and Test Equipment 2 distillation apparatuses described above are employed. The process to obtain the 220-240° C. fraction was similar to the one described above used for obtaining the other distilled fractions, e.g. the 230-260° C. fraction. Details concerning the resulting composition are set forth in the following Table 26.

TABLE 26

Composition of 220-240° C. fraction

| Component | Carbon number | Isomer | wt-% |
|---|---|---|---|
| <C3 | 2 | iP | 0.00 |
| Propane | 3 | nP | 0.00 |
| iso-C4 | 4 | iP | 0.00 |
| n-Butane | 4 | nP | 0.00 |
| iso-C5 | 5 | iP | 0.00 |
| n-pentane | 5 | nP | 0.00 |
| iso-C6 | 6 | iP | 0.00 |
| n-hexane | 6 | nP | 0.00 |
| iso-C7 | 7 | iP | 0.00 |
| n-heptane | 7 | nP | 0.00 |
| iso-C8 | 8 | iP | 0.00 |
| n-octane | 8 | nP | 0.00 |
| iso-C9 | 9 | iP | 0.00 |
| n-nonane | 9 | nP | 0.00 |
| iso-C10 | 10 | iP | 0.00 |
| n-Decane | 10 | nP | 0.00 |
| C11-paraffins; di/tri-methyl- | 11 | iP-di/tri-me | 0.03 |
| C11-paraffins; methyl- | 11 | iP-me | 0.12 |

TABLE 26-continued

Composition of 220-240° C. fraction

| Component | Carbon number | Isomer | wt-% |
|---|---|---|---|
| C12-isoparaffins, tri+ -methyl- | 12 | iP-trime+ | 0.05 |
| n-Undecane | 11 | nP | 0.13 |
| C12-paraffins; di/tri-methyl- | 12 | iP-di/tri-me | 1.89 |
| C12-isoparaffins; mono-methyl- | 12 | iP-me | 5.07 |
| C13-isoparaffins, tri+ -methyl- | 13 | iP-trime+ | 1.63 |
| n-Dodecane | 12 | nP | 1.91 |
| C13-paraffins; di/tri-methyl- | 13 | iP-di/tri-me | 16.77 |
| C13-isoparaffins, mono-methyl- | 13 | iP-me | 20.89 |
| C14-isoparaffins, tri+ -methyl- | 14 | iP-trime+ | 5.68 |
| n-Tridecane | 13 | nP | 3.14 |
| C14-paraffins; di/tri-methyl- | 14 | iP-di/tri-me | 21.72 |
| C14-isoparaffins, mono-methyl- | 14 | iP-me | 10.88 |
| C15-isoparaffins, tri+ -methyl- | 15 | iP-trime+ | 2.73 |
| n-Tetradecane | 14 | nP | 0.84 |
| C15-paraffins; di/tri-methyl- | 15 | iP-di/tri-me | 4.16 |
| C15-isoparaffins, mono-methyl- | 15 | iP-me | 1.45 |
| C16-isoparaffins, tri+ -methyl- | 16 | iP-trime+ | 0.36 |
| n-Pentadecane | 15 | nP | 0.08 |
| C16-paraffins; di/tri-methyl- | 16 | iP-di/tri-me | 0.34 |
| C16-isoparaffins, mono-methyl- | 16 | iP-me | 0.10 |
| C17-isoparaffins tri+ -methyl- | 17 | iP-trime+ | 0.01 |
| n-Hexadecane | 16 | nP | 0.00 |
| C17-paraffins; di/tri-methyl- | 17 | iP-di/tri-me | 0.02 |
| C17-isoparaffins, mono-methyl- | 17 | iP-me | 0.00 |
| C18-isoparaffins, tri+ -methyl- | 18 | iP-trime+ | 0.00 |
| n-Heptadecane | 17 | nP | 0.00 |
| C18-paraffins; di/tri-methyl- | 18 | iP-di/tri-me | 0.00 |
| C18-isoparaffins, mono-methyl- | 18 | iP-me | 0.00 |
| C19-isoparaffins, tri+ -methyl- | 19 | iP-trime+ | 0.00 |
| n-Octadecane | 18 | nP | 0.00 |
| C19-isoparaffins; di/tri-methyl- | 19 | iP-di/tri-me | 0.00 |
| C19-isoparaffins, mono-methyl- | 19 | iP-me | 0.00 |
| C20-isoparaffins, tri+ -methyl- | 20 | iP-trime+ | 0.00 |
| n-Nonadecane | 19 | nP | 0.00 |
| C20-isoparaffins; di/tri-methyl- | 20 | iP-di/tri-me | 0.00 |
| C20-isoparaffins, mono-methyl- | 20 | iP-me | 0.00 |
| C21-isoparaffins, tri+ -methyl- | 21 | iP-trime+ | 0.00 |
| Eicosan | 20 | nP | 0.00 |
| C21-isoparaffins; di/tri-methyl- | 21 | iP-di/tri-me | 0.00 |
| C21-isoparaffins, mono-methyl- | 21 | iP-me | 0.00 |
| C22-isoparaffins, tri+ -methyl- | 22 | iP-trime+ | 0.00 |
| Heneicosan | 21 | nP | 0.00 |
| C22-isoparaffins; di/tri-methyl- | 22 | iP-di/tri-me | 0.00 |
| C22-isoparaffins, mono-methyl- | 22 | iP-me | 0.00 |
| C23-isoparaffins; tri+ -methyl- | 23 | iP-trime+ | 0.00 |
| Docosan | 22 | nP | 0.00 |
| C23-isoparaffins; di/tri-methyl- | 23 | iP-di/tri-me | 0.00 |
| C23-isoparaffins, mono-methyl- | 23 | iP-me | 0.00 |
| C24-isoparaffins, tri+ -methyl- | 24 | iP-trime+ | 0.00 |
| Tricosane | 23 | nP | 0.00 |
| C24-isoparaffins; di/tri-methyl- | 24 | iP-di/tri-me | 0.00 |
| C24-isoparaffins, mono-methyl- | 24 | iP-me | 0.00 |
| C25-isoparaffins, tri+ -methyl- | 25 | iP-trime+ | 0.00 |
| Tetracosane | 24 | nP | 0.00 |
| C25-C29 | C25-C29 | iP | 0.00 |
| C30-C36 | C30-C36 | iP | 0.00 |
| >C36 | >C36 | iP | 0.00 |
| Total | | | 100.00 |

In Table 26, "iP" refers to isoparaffins, and "me" refers to methylene groups, e.g., "iP-me" refers to an isoparaffin with one methylene group (branch).

The various fractions obtained by separation processes can be used in various applications. For example, a fraction rich in C14-C16 can be used in, for example, oils, lubricants, waxes, personal care, cosmetics, pharmaceuticals, detergents, plastics and additives, coatings and functional fluids, surfactants and intermediates such as chlorinated or sulphonated paraffins used as is or for the production of, e.g., plasticizers. A fraction rich in C16-C18 can be used in, for example, oils, lubricants, waxes, personal care, cosmetics, pharmaceuticals, detergents, plastics and additives, coatings and functional fluids, surfactants and intermediates such as chlorinated or sulphonated paraffins used as is or for the production of, e.g., plasticizers. A fraction rich in C18 can be used in, for example, oils, lubricants, waxes, personal care, cosmetics, pharmaceuticals, detergents, plastics and additives, coatings and functional fluids, surfactants and intermediates such as chlorinated or sulphonated paraffins used as is or for the production of, e.g., plasticizers.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

CITED DOCUMENTS

The following is a list of the cited documents mentioned above:

[13] "ASTM Standard D7345, 2008, "Distillation of Petroleum Products at Atmospheric Pressure (Micro Distillation Method)"," ASTM International, West Conshohocken, Pa., 2008. 15 p.

[15] "ASTM Standard D86, 2011a, "Distillation of Petroleum Products at Atmospheric Pressure"," ASTM International, West Conshohocken, Pa., 2011. 27 p.

[20] "ASTM Standard D2887, 2008, "Boiling Range Distribution of Petroleum Fractions by Gas Chromatography"," ASTM International, West Conshohocken, Pa., 2008. 20 p.

[39] G. Wypych, "Solvents, Industrial," in *Kirk-Othmer Encyclopedia of Chemical Technology*.: John Wiley & Sons, Inc., 2006, vol. 23, pp. 1-41. [Online]. www.onlinelibrary.wiley.com

[40] G. Wypych, "Basic Physical and Chemical Properties of Solvents," in *Handbook of Solvents*, G. Wypych, Ed. Toronto: Chem Tec Publishing, 2001, ch. 2.3, pp. 42-63. [Online]. www.knovel.com

[43] "ASTM Standard D5950, 2007, "Pour Point of Petroleum Products (Automatic Tilt Method)"," ASTM International, West Conshohocken, Pa., 2007. 5 p.

[44] "ASTM Standard D5771, 2010, "Cloud Point of Petroleum Products (Optical Detection Stepped Cooling Method)"," ASTM International, West Conshohocken, Pa., 2010. 6 p.

[48] "ASTM Standard D445, 2009, "Kinematic Viscosity of Transparent and Opaque Liquids (and Calculation of Dynamic Viscosity)"," ASTM International, West Conshohocken, Pa., 2009. 10 p.

[49] "ASTM Standard D2270, 2010, "Calculating Viscosity Index from Kinematic Viscosity at 40 and 100° C."," ASTM International, West Conshohocken, Pa., 2010. 6 p.

[54] C. Bordes, V. Fréville, E. Ruffin, P. Marote, J. Y. Gauvrit, S. Briançon and P. Lantéri, "Determination of poly(ε-caprolactone) solubility parameters: Application to solvent substitution in a microencapsulation process," *International Journal of Pharmaceutics*, vol. 383, no. 1-2, pp. 236-243, 2010.

[55] W. Andrew, *PDL HANDBOOK SERIES: Chemical Resistance of Thermoplastics*, W. Woishnis and S. Ebnesajjad, Eds. Waltham, USA: Elsevier Inc., pp. XV-LI, 2012. [Online]. http://books.google.com

[62] S. J. Kim, S. J. Park, and S. I. Kim, "Swelling behavior of interpenetrating polymer network hydrogels composed of poly(vinyl alcohol) and chitosan," *Reactive & Functional Polymers*, vol. 55, pp. 53-59, 2003.

[68] Q. Li, D. L. Feke, and I. M. Zloczower, "Comparison of stability and dispersion characteristics of organic pigment agglomerates," *Powder Technology*, vol. 92, pp. 17-24, 1997.

[80] "ASTM Standard D93, 2008, "Flash Point by Pensky-Martens Closed Cup Tester"," ASTM International, West Conshohocken, Pa., 2008. 18 p.

[81] "ASTM Standard D56, 2010, "Flash Point by Tag Closed Cup Tester"," ASTM International, West Conshohocken, Pa., 2010. 11 p.

[82] "ASTM Standard D611, 2007, "Aniline Point and Mixed Aniline Point of Petroleum Products and Hydrocarbon Solvents"," ASTM International, West Conshohocken, Pa., 2007. 7 p.

[83] "ASTM Standard D4052, 2011, "Density, Relative Density, and API Gravity of Liquids by Digital Density Meter"," ASTM International, West Conshohocken, Pa., 2011. 8 p.

[85] "ASTM Standard D2624, 2009, "Electrical Conductivity of Aviation and Distillate Fuels"," ASTM International, West Conshohocken, Pa., 2009. 11 p.

[88] "ASTM Standard D6045, 2009, "Color of Petroleum Products by the Automatic Tristimulus Method"," ASTM International, West Conshohocken, Pa., 2009. 8 p.

[89] "ASTM Standard D1218, 2007, "Refractive Index and Refractive Dispersion of Hydrocarbon Liquids"," ASTM International, West Conshohocken, Pa., 2007. 7 p.

[92] "ASTM Standard D2710, 2009, "Bromine Index of Petroleum Hydrocarbons by Electrometric Titration"," ASTM International, West Conshohocken, Pa., 2009. 4 p.

[95] "ASTM Standard D5453, 2009, "Determination of Total Sulfur in Light Hydrocarbons, Spark Ignition Engine Fuel, Diesel Engine Fuel, and Engine Oil by Ultraviolet Fluorescence"," ASTM International, West Conshohocken, Pa., 2009. 10 p.

[97] C. Chiyoda, E. C. D. Peixoto, A. J. A. Meirelles, and C. E. C. Rodrigues, "Liquid-Liquid equilibria for systems composed of refined soybean oil, free fatty acids, ethanol, and water at different temperatures," *Fluid Phase Equilibria*, vol. 299, pp. 141-147, 2010.

[98] ALZAID Chemical Compatibility Test Kit. [Online]. www.alzet.com/downloads/alzaidspecs.pdf, 15 Mar. 2013.

[99] Orgasol powders: Arkema Inc. [Online]. http://www.arkema-inc.com/literature/pdf/92.pdf, 15 Mar. 2013.

[100] "ASTM Standard D1401, 2010, "Water Separability of Petroleum Oils and Synthetic Fluids"," ASTM International, West Conshohocken, Pa., 2010. 5 p.

[101] M. Daaou and D. Bendedouch, "Water pH and surfactant addition effects on the stability of an Algerian crude oil emulsion," *Journal of Saudi Chemical Society*, vol. 16, pp. 333-337, 2012.

[102] Berol 791: AkzoNobel Fabric & Cleaning. [Online]. http://sc.akzonobel.com/en/fabric-cleaning/Pages/product-detail.aspx?prodID=8242, 7 May 2013.

[103] SIMULSOL 165: SEPPIC. [Online]. http://www.seppic.com/cosmetic/emulsifier/simulsol-165-@/view-361-seproduit.html;jsessionid=xSYB9LuYcjgHYDGOpgH4w, 7 May 2013.

[104] Zschimmer & Schwarz: Technical datasheet MULSIFAN CB Oil/water emulsifier for cosmetics. [Online]. http://www.zschimmer-schwarz.com/MULSIFAN CB/si-mon/zschimmerschwarz/media/site/downloads/merkblatt/1_S_S_ENG_4255_10_2_370.pdf, 7 May 2013.

[105] J. Viyoch., Surfa Tech-Technology Library-Emulsions. [Online]. http://www.surfatech.com/pdfs/emulsions.pdf, 7 May 2013.

[106] ASTM International. [Online].http://www.astm.org/Standard/index.shtml, 17 Jun. 2013.

[107] Y. Natsume, T. Minakata, and T. Aoyagi, "Structures and electronic properties of thin-films of polycyclic aromatic hydrocarbons," *Thin Solid Films*, vol. 517, pp. 3005-3010, 2009.

[108] "ISO 6297:1997 Petroleum products—Aviation and distillate fuels—Determination of electrical conductivity," International Organization for Standardization, Geneva, 1997.

[109] Dinonylnaphthalene Category: Screening-Level Hazard Characterization of High Production Volume Chemicals, U.S. environmental Protection Agency. [Online]. http://www.epa.gov/chemrtk/hpvis/hazchar/Category_Dinonylnaphthalene_M arch_2012.pdf, 11 Jun. 2013.

[110] T. Kasza and J. Hancsok, "Investigation of Fuel Components Produced by The Isomerization of Bio-paraffin Mixtures," *Hungarian Journal of Industrial Chemistry Veszprem*, vol. 39, pp. 121-126, 2011.

What is claimed is:

1. A composition, comprising:
   40-50 wt-% C14 isoparaffins, based on the total weight of the composition, and
   35-45 wt-% C15 isoparaffins, based on the total weight of the composition,
   wherein the C14 and C15 isoparaffins are produced from a biological raw material,
   wherein the total isoparaffinic content of the composition is more than 93 wt-%, based on the total weight of the composition.

2. The composition according to claim 1, wherein the composition comprises 45-50 wt-% C14 isoparaffins, and 40-45 wt-% C15 isoparaffins, based on the total weight of the composition.

3. The composition according to claim 1, wherein the composition comprises less than 9 wt-% C13 and lighter paraffins and less than 7 wt-% C16 and heavier paraffins, based on the total weight of the composition.

4. The composition according to claim 1, wherein the composition comprises less than 5 wt-% C13 and lighter paraffins and less than 3 wt-% C16 and heavier paraffins, based on the total weight of the composition.

5. The composition according to claim 1, wherein the total aromatic hydrocarbon content of the composition is less than 1500 ppm weight basis.

6. The composition according to claim 1, wherein the total aromatic hydrocarbon content of the composition is less than 1300 ppm weight basis.

7. The composition according to claim 1, wherein the total aromatic hydrocarbon content of the composition is less than 500 ppm weight basis.

8. The composition according to claim 1, wherein the C14 and C15 paraffins are produced by a process comprising hydrodeoxygenation and isomerization of a biological raw material.

9. The composition according to claim 1, wherein the composition has a boiling point in a range of 240° C. to 260° C.

10. The composition according to claim 1, wherein the composition has a boiling point in a range of 245° C. to 255° C.

11. The composition according to claim 1, wherein the composition is suitable for use as a solvent or a solvent component.

12. The composition according to claim 1, wherein the composition is in liquid form.

13. The composition according to claim 1, wherein the composition is an emulsion.

14. The composition according to claim 1, wherein the composition is suitable for use in a coating, paint, lacquer, varnish, polish, ink, adhesive, sealant, resin, plastic, catalyst, cleaning composition, peroxide desensitizer, pigment dispersion, carrier fluid for an active ingredient, antioxidant, biocide, insecticide, air freshener, crop protection composition, detergent, grease removal composition, dry cleaning composition, cosmetic, personal care composition, pharmaceutical, extender in a dental impression material, vaccine, food ingredient, flavor composition, fragrance, natural oil extraction, oil field chemical, drilling mud composition, extraction process composition, plasticizer for elastomer, paper processing chemical, lubricant, functional fluid, transformer oil, metal working composition, rolling or cutting fluid, water treatment composition, wood treatment composition, construction chemical, mould release material, explosive, mining chemical, solvent extraction composition, fuel component, heating oil, lamp oil, or a combination thereof.

15. A process for producing the composition according to claim 1, the process comprising:
   conducting hydrodeoxygenation and isomerization reactions of a biological raw material; and
   conducting a separation process of the resulting material, wherein the separation process includes fractionation by distillation to produce a composition comprising:
   40-50 wt. % $C_{14}$ isoparaffins, based on the total weight of the composition, and
   35-45 wt. % $C_{15}$ isoparaffins, based on the total weight of the composition,
   wherein the $C_{14}$ and $C_{15}$ isoparaffins are produced from a biological raw material,
   wherein the total isoparaffinic content of the composition is more than 93 wt. % based on the total weight of the composition.

16. The composition according to claim 1, wherein the total isoparaffinic content of the composition is more than 97 wt-%, based on the total weight of the composition.

* * * * *